United States Patent
Hallett et al.

(10) Patent No.: US 11,164,329 B2
(45) Date of Patent: Nov. 2, 2021

(54) MULTI-CHANNEL SPATIAL POSITIONING SYSTEM

(71) Applicant: INPIXON, Palo Alto, CA (US)

(72) Inventors: James Francis Hallett, Palo Alto, CA (US); Kirk Arnold Moir, Palo Alto, CA (US)

(73) Assignee: INPIXON, Palo Alto, CA (US)

( * ) Notice: Subject to any disclaimer, the term of this patent is extended or adjusted under 35 U.S.C. 154(b) by 0 days.

(21) Appl. No.: 16/668,180

(22) Filed: Oct. 30, 2019

(65) Prior Publication Data

US 2020/0143561 A1 May 7, 2020

Related U.S. Application Data

(60) Provisional application No. 62/754,446, filed on Nov. 1, 2018.

(51) Int. Cl.
*G06T 7/73* (2017.01)
*G06K 9/00* (2006.01)
(Continued)

(52) U.S. Cl.
CPC ............ *G06T 7/73* (2017.01); *G06K 9/00348* (2013.01); *G06K 9/00771* (2013.01);
(Continued)

(58) Field of Classification Search
CPC . G06T 7/73; G06T 7/292; G06T 2207/20084; G06T 7/11; G06T 7/277;
(Continued)

(56) References Cited

U.S. PATENT DOCUMENTS 8,890,685 B1   11/2014   Sookman
9,234,965 B2   1/2016    Venkatraman
(Continued)

OTHER PUBLICATIONS

H. Medeiros, J. Park and A. Kak, "Distributed Object Tracking Using a Cluster-Based Kalman Filter in Wireless Camera Networks," in IEEE Journal of Selected Topics in Signal Processing, vol. 2, No. 4, pp. 448-463, Aug. 2008, doi: 10.1109/JSTSP.2008.2001310. (Year: 2008).*

(Continued)

*Primary Examiner* — Michael Robert Cammarata
(74) *Attorney, Agent, or Firm* — Pillsbury Winthrop Shaw Pittman, LLP

(57) ABSTRACT

A method includes acquiring a set of images from a plurality of cameras in a monitored environment, detecting a first entity based on the set of images, and determining a first set of locations of the first entity based on locations of the first entity in the set of images. The method also includes acquiring sensor measurements from a plurality of sensors and determining a second set of locations of the first entity based on the sensor measurements. The method also includes determining whether the first set of locations should be associated with the second set of locations based on a confidence factor, and, in response to determining that the first and second set of locations should be associated, determining a sequence of locations of the first entity through the monitored environment.

44 Claims, 4 Drawing Sheets

(51) Int. Cl.
| | |
|---|---|
| *G06T 7/292* | (2017.01) |
| *G06T 7/11* | (2017.01) |
| *G06T 7/277* | (2017.01) |
| *G08B 13/196* | (2006.01) |
| *H04N 5/247* | (2006.01) |
| *G06K 9/62* | (2006.01) |
| *G06T 7/13* | (2017.01) |
| *G08B 5/22* | (2006.01) |
| *G01S 5/18* | (2006.01) |
| *G01J 5/10* | (2006.01) |
| *G01N 33/00* | (2006.01) |
| *G01S 5/02* | (2010.01) |

(52) U.S. Cl.
CPC ........... *G06K 9/6201* (2013.01); *G06K 9/628* (2013.01); *G06K 9/6256* (2013.01); *G06T 7/11* (2017.01); *G06T 7/13* (2017.01); *G06T 7/277* (2017.01); *G06T 7/292* (2017.01); *G08B 5/22* (2013.01); *G08B 13/196* (2013.01); *H04N 5/247* (2013.01); *G01J 5/10* (2013.01); *G01N 33/0047* (2013.01); *G01S 5/0257* (2013.01); *G01S 5/18* (2013.01); *G06T 2207/20084* (2013.01); *G06T 2207/30232* (2013.01)

(58) Field of Classification Search
CPC ........... G06K 9/00771; G06K 9/00348; G01S 5/0257
See application file for complete search history.

(56) References Cited

U.S. PATENT DOCUMENTS

| | | | | |
|---|---|---|---|---|
| 9,582,720 | B2 | 2/2017 | Gupta et al. | |
| 9,785,857 | B2* | 10/2017 | Moshfeghi | ............... G06K 9/46 |
| 9,989,624 | B2 | 6/2018 | Ryan et al. | |
| 10,111,197 | B2 | 10/2018 | Ronen | |
| 2011/0134240 | A1* | 6/2011 | Anderson | ................ G06T 7/73 |
| | | | | 348/143 |
| 2012/0046044 | A1* | 2/2012 | Jamtgaard | ............ G01S 5/0257 |
| | | | | 455/456.1 |
| 2013/0101159 | A1* | 4/2013 | Chao | ................. G06K 9/00771 |
| | | | | 382/103 |
| 2013/0212094 | A1 | 8/2013 | Naguib et al. | |
| 2014/0169352 | A1* | 6/2014 | Moir | ..................... H04W 4/023 |
| | | | | 370/338 |
| 2016/0274215 | A1 | 9/2016 | Edge et al. | |
| 2017/0053419 | A1* | 2/2017 | Moshfeghi | ............. G06T 7/292 |
| 2017/0148241 | A1* | 5/2017 | Kerning | ............... G08B 25/016 |
| 2017/0187991 | A1* | 6/2017 | Toros | .................... G01S 5/0257 |
| 2017/0248428 | A1 | 8/2017 | Cho et al. | |
| 2017/0332054 | A1* | 11/2017 | Hallett | ................... H04N 21/83 |
| 2018/0089505 | A1* | 3/2018 | El-Khamy | ............... G06T 7/73 |
| 2018/0252528 | A1* | 9/2018 | Zhuang | ................ G01C 21/165 |
| 2019/0019050 | A1* | 1/2019 | Roblek | ..................... G06N 3/08 |
| 2019/0158982 | A1* | 5/2019 | Farnham | ............... H04W 4/025 |
| 2019/0172223 | A1* | 6/2019 | Vajda | ................... G06K 9/4633 |
| 2019/0182790 | A1* | 6/2019 | Kothari | ................... G06T 7/20 |
| 2019/0265714 | A1* | 8/2019 | Ball | ....................... G05D 1/024 |
| 2020/0089990 | A1* | 3/2020 | Xu | ......................... G06Q 10/10 |
| 2020/0134395 | A1* | 4/2020 | Yang | ....................... G06T 7/73 |

OTHER PUBLICATIONS

Efficient integration of RSSI for tracking using Wireless Camera Networks De San Bernabe, A.; Martinez-de Dios, J. R.; Ollero, A . . . Information Fusion36: 296-312. Elsevier B.V. (Jul. 2017) (Year: 2017).*

Mittal, "Adapting Convolutional Neural Networks for Indoor Localization with Smart Mobile Devices", GLSVLSI'18, May 23-25, 2018, Chicago, IL, USA. (Year: 2018).*

Multi-Sensor Fusion Tracking Using Visual Information and WI-FI Location Estimation T. Miyaki;T. Yamasaki;K. Aizawa 2007 First ACM/IEEE International Conference on Distributed Smart Cameras (Year: 2007).*

Jiao, "A Smartphone Camera-Based Indoor Positioning Algorithm of Crowded Scenarios with the Assistance of Deep CNN", Sensors 2017, 17, 704; doi: 10.3390/s17040704 (Year: 2017).*

* cited by examiner

MULTI-CHANNEL SPATIAL POSITIONING SYSTEM

CROSS-REFERENCE TO RELATED APPLICATIONS

This patent claims the benefit of U.S. Provisional Patent Application 62/754,446, filed 1 Nov. 2018, titled "A MULTI-SENSOR SYSTEM FOR MONITORING CROWDS OF INDIVIDUALS." The entirety content of each aforementioned patent filing is hereby incorporated by reference.

BACKGROUND

1. Field

This disclosure relates generally to positioning systems and, more particularly, to multi-sensor positioning systems.

2. Background

Understanding visitor behavior is useful for the design, operation and optimization of public or semi-public spaces. Visitor behavior information is valuable to various stakeholders of the space, such as an owner of the space, an operator of the space, security personnel and merchant staff operating in the space, or the like.

Existing computer systems to determine indoor positions of visitors suffer from a number of challenges. Some systems require the visitor to wear a tracking device, but these arrangements are often untenable in public places, where people are unwilling to wear such devices. Some systems merely afford low-resolution, sparse indications of position, like card-based electronic door access controls.

SUMMARY

The following is a non-exhaustive listing of some aspects of the present techniques. These and other aspects are described in the following disclosure.

Some aspects include a process that includes acquiring, using a computer system, a set of images from a plurality of cameras, wherein: each of the plurality of cameras have a different respective field of view, and at least part of the fields of view are of a monitored environment; detecting and localizing, using the computer system, in at least some of the set of images, a first entity moving through the monitored environment; determining, using the computer system, a first set of locations within the monitored environment of the first entity based on locations of the first entity in the set of images, wherein each of the first set of locations is associated with an image acquisition time; acquiring, using the computer system, a set of sensor measurements of the monitored environment from a plurality of sensors, the plurality of sensors being different from the plurality of cameras; determining, using the computer system, a second set of locations within the monitored environment of the first entity based on the set of sensor measurements, wherein each of the second set of locations is associated with a sensor measurement time; determining, using the computer system, whether the first set of locations should be associated with the second set of locations based on a set of confidence factors calculated based on the first set of locations and the second set of locations, the set of confidence factors being indicative of the second set of locations being locations of the first entity and not another entity; in response to determining that the first set of locations should be associated with the second set of locations, determining, using the computer system, a sequence of locations of the first entity through the monitored environment; and storing, using the computer system, the sequence of locations in a computer-readable media in communication with the computer system.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
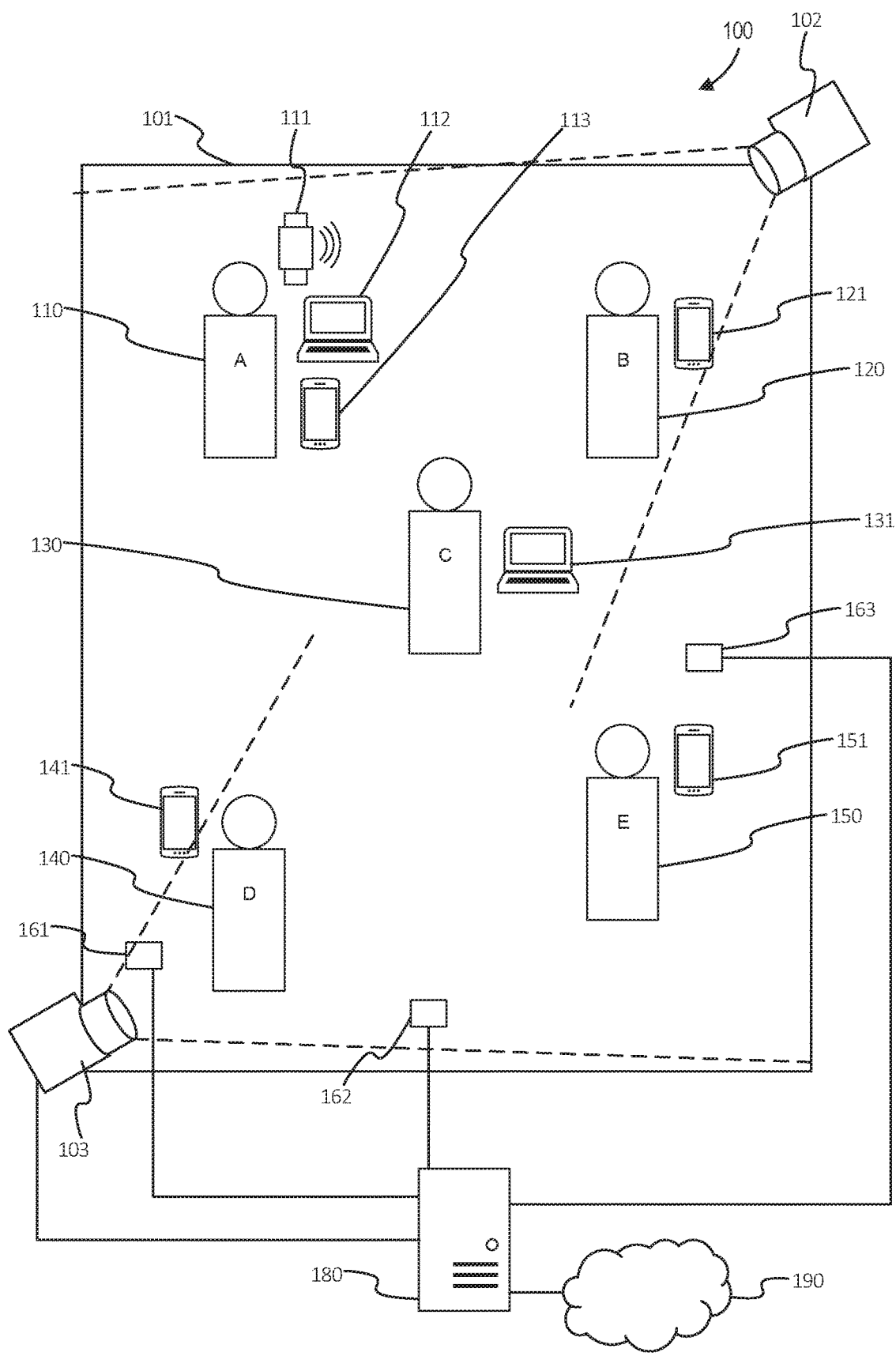
FIG. 1 is a diagram of a monitored environment in which various entities may be tracked using the present techniques, in accordance with some embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of indoor positioning. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Many existing computer vision techniques are not well suited for tracking the positions objects or other physical entities that move through a monitored environment. Often, cameras are relatively few in number and have fields of view that do not fully cover the environment. Blind spots are common. In many cases, even when an area is within a field of view, limited resolution and lighting impair tracking accuracy. These issues are often aggravated when multiple entities are tracked concurrently, as it can be difficult to determine when objects detected by two different cameras are the same object, for instance in different locations after moving.

Some embodiments determine a sequence of locations of a set of physical entities (e.g., people) in a monitored environment (e.g., a room or building) based on multiple channels of data, such as images from cameras and data from other sensors (e.g., wireless signal triangulation and others described below). Some embodiments may first detect the presence of a physical entity in a monitored environment and track locations of the physical entity over time based on images and other sensor data. In some embodiments, each physical entity may be associated with one or more attributes by which different, concurrently-present entities are distinguished from one another in sensor data. Some embodiments may then associate a subset of the sensor data with the physical entity to determine a time-ordered sequence of locations associated with the physical entity. Some embodiments determine a time-ordered sequence of locations based on the combined sensor data from a plurality of input channels. Furthermore, some embodiments may more efficiently and accurately (relative to conventional computer vision techniques) infer or otherwise determine the sequence of locations by determining a boundary based on how far a physical entity can move in a given amount of time and using the boundary to determine whether different detected entities are based on a same physical entity. Some embodiments may use the sequence of locations associated with an entity or other time-ordered values associated with the entity to determine whether the entity is performing or not performing an activity, moving to a different location, demonstrating behavior pattern, or the like.

Some embodiments use a tracking method that incorporates multi-channel data to determine locations of entities as they move through a monitored environment. As a result, it is expected that the accuracy of tracking may be increased relative to other computer vision techniques. Such tracking may be of use for crowd control, counting, visit frequency and traffic pattern determination for tracking a variety of physical entities, where physical entities may include people, animals with electronic collars, drones, robots, or the like. Such multi-channel tracking may increase accuracy when tracking visit counts, the visit frequencies of visitors, or traffic patterns during visits.

FIG. 1 is a diagram of a monitored environment in which various entities may be tracked using the present techniques, in accordance with some embodiments. FIG. 1 illustrates an entity-tracking system 100 that is used to monitor a monitored environment 101. The entity-tracking system 100 includes a set of sensors, where the set of sensors may include a set of cameras or other types of sensors to capture data having a plurality of input channels, where the entity-tracking system 100 may track an entity over time based on the data. In some embodiments, the set of sensors may include at least two sensors, three sensors, five sensors, or the like. The set of cameras may include a first camera 102 and a second camera 103. Each camera of the set of cameras may have an associated field of view of some or all of the monitored environment 101. For example, the first camera 102 may acquire a set of images directed to a first field of view of the monitored environment 101 that includes a first physical entity 110, a second physical entity 120, and a third physical entity 130, where entities may be detected based on images of the physical entities 110, 120, and 130. The second camera 103 may acquire a set of images directed to a second field of view of the monitored environment 101 of the third physical entity 130, a fourth physical entity 140, and a fifth physical entity 150, where entities may be detected based on images of the physical entities 130, 140, and 150. In some embodiments, a first entity may be detected based on images from the first camera 102 and a second entity may be detected based on images from the second camera 103, and, as further described below, a comparison of attributes or values associated with the first entity or second entity may result in a determination that the first and second entities are based on the same third physical entity 130. In some embodiments, a field of view associated with a camera may change based on a camera zoom, change in camera orientation, or other change in a camera parameter. In some embodiments, the set of cameras may be fixed to a structure or otherwise inhibited from changing the boundaries of their fields of view during operations, where keeping a camera fixed may increase entity detection efficiency and accuracy. In some embodiments, the set of cameras may be attached to a moving object, such as a vehicle or drone. Furthermore, in some embodiments, a set of cameras used in a monitored environment may have non-overlapping fields of view, where the methods disclosed herein may allow for entity tracking across disconnected fields of view. The image output of these cameras may be sent to an on-premise server 180 or cloud computing system 190.

Either or both the on-premise server 180 or a cloud computing system 190 may perform one or more of the operations described further below. Operations performed on the set of images or other sensor measurements may be used to detect entities and determine a set of locations for the entities, where a location may be a specific spatial coordinate or a spatial region. A specific spatial coordinate may include latitude and longitude coordinates, a cartesian coordinate in a monitored space relative to a reference position, a coordinate in a radial or polar coordinate system, or the like. A spatial region may include a region of the monitored environment observed in a camera's field of view, a sensing volume of a sensor, a specific room in a building, or the like.

In some embodiments, the entity-tracking system may include a set of sensors different from the set of cameras distributed throughout the monitored environment 101 to acquire sensor measurements. A sensor measurement may have an associated sensor measurement time, an input channel, and a set of sensor measurement values. A sensor measurement time may be associated with the sensor measurement, and may include a time of physical measurement, a time during which the measurement was recorded in a memory storage, a time during which the measurement was processed, a time during which the measurement was transmitted to a computing device, or the like. For example, a sensor measurement may have an associated sensor measurement time equal to when the sensor measurement was first recorded, an associated input channel of "wireless signal," and a set of sensor measurement values that include associated signal strength values. The set of sensors may include one or more electronic emission sensors (EES), cameras, temperature sensors, chemical sensors (also known as "scent sensors," like miniaturized mass spectrometers), motion sensors, ultrasonic sound sensors, lidar sensors, radio detection and ranging (RADAR) sensors, or the like. Sensor data may include data directly acquired from a sensor or processed results of sensor data. For example, sensor data may include the video feed from a camera, signals acquired by an EES, or temperature measurements from a temperature sensor. Furthermore, in some embodiments, different types of sensors may be attached to each other.

In some embodiments, the set of EES 161-163 may acquire, measure, or interpret one or more types of wireless signals, such as Wi-Fi signals, cellular signals, Bluetooth signals, ultra-wideband signals, and various other types of wireless signals, where an EES may have one or more antennas to receive and emit wireless signals. Such wireless signals may be emitted by mobile computing devices carried by the entities shown in FIG. 1. For example, the first physical entity 110 may carry a first set of mobile computing devices 111-113, the physical second entity 120 may carry a fourth mobile computing device 121, the third physical entity 130 may carry a fifth mobile computing device 131, the fourth physical entity 140 may carry a sixth mobile computing device 141, and the fifth physical entity 150 may carry a seventh mobile computing device 151. In some embodiments, the set of EES 161-163 may emit one or more inducing signals to induce wireless communication components such as RFID tags to emit wireless signals. Alternatively, or in addition, the set of EES 161-163 may passively receive wireless signals that were not induced by an inducing signal. In some embodiments, the set of EES 161-163 may be used to acquire sensor measurements such as signal parameters or data transmitted in the signal, where the device data or signal measurements determine a device position based on signals emitted by a mobile computing device. A set of EES may acquire data that can be used to determine the location of a mobile computing device based on various positioning methods and send the data to a server, as described further below. For example, each of the set of EES 161-163 may measure received signal strength indicator (RSSI) values at a plurality of positions and transmit the values to the on-premise server 180. The set of EES 161-163 may be connected to the on-premise server 180 via a communications interface such as a cable modem, fiber optic device, wireless communication device, or the like.

In some embodiments, the on-premise server 180 or cloud computing system 190 may determine a device location using various positioning methods, as described further below. In some embodiments, the on-premise server 180 may include a database to persistently store and retrieve sensor measurements, images, measurement times, or other data. Alternatively, or in addition, the on-premise server 180 may be in communication with an external database, such as an external database of the cloud computing system 190, to persistently store and retrieve sensor measurements, images, measurement times, or other data. In some embodiments, a database may store information about the venues registered with the entity-tracking system and may include a one or more of a venue name, venue contact information, security credentials, street address, global address expressed in latitude and longitude and possible site-specific information. In some embodiments, a database may store information associated one or more various sensors in an entity-tracking system or data collected by the entity-tracking system. For example, a server may store values to and retrieve values from a database that includes an assigned sensor name, specific messages sent to and from a sensor, sensor IP addresses, mobile computing device identifiers, detected entities, a venue appearance history, or the like.

Conventional attempts to apply deep learning and prediction operations to video surveillance systems may be insufficient due to the high computational cost of these conventional deep learning methods. However, as further described below, these issues may be mitigated by some embodiments, where the set of cameras may include a memory storage or processor for the training and use of one or more neural networks. For example, the first camera 102 may include a processor to perform classification or tracking operations using a convolutional neural network, where results of the classification or tracking operation performed by the first camera 102 may be transmitted to the on-premise server 180 or cloud computing system 190. By applying a neural network operation at the sensor level and transmitting results to other computing devices, an entity-tracking system may increase the efficiency and accuracy of real-time tracking relative to conventional deep learning surveillance systems. However, this is not to suggest that all embodiments include sensor with processors or memory storage devices, as the systems and operations described herein may be implemented using sensors that do not include processors capable of training or using neural networks.

Figure 2:
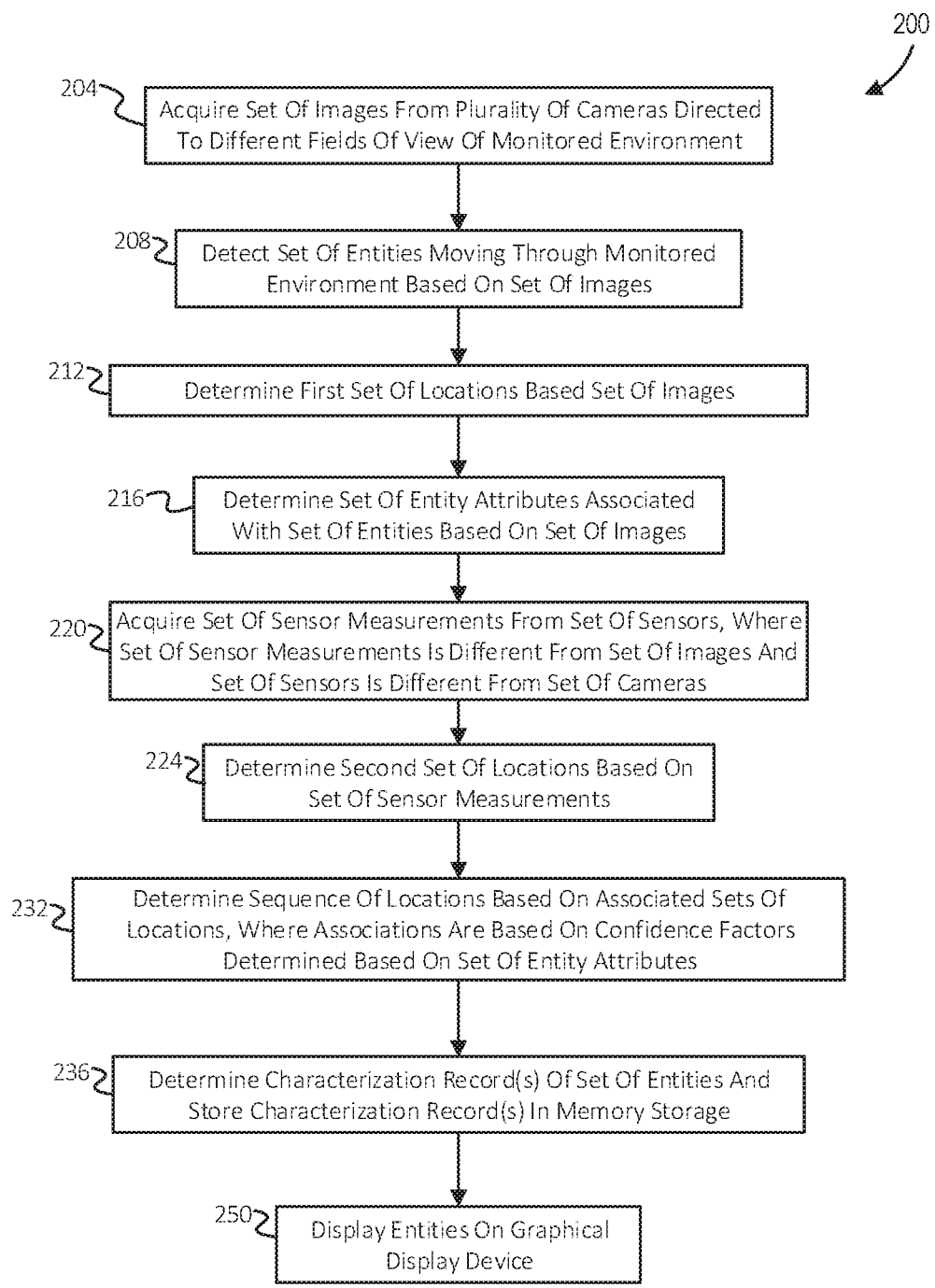
FIG. 2 is a flowchart of operations to determine a sequence of locations based on a set of images and sensor measurements, in accordance with some embodiments.
Figure 3:
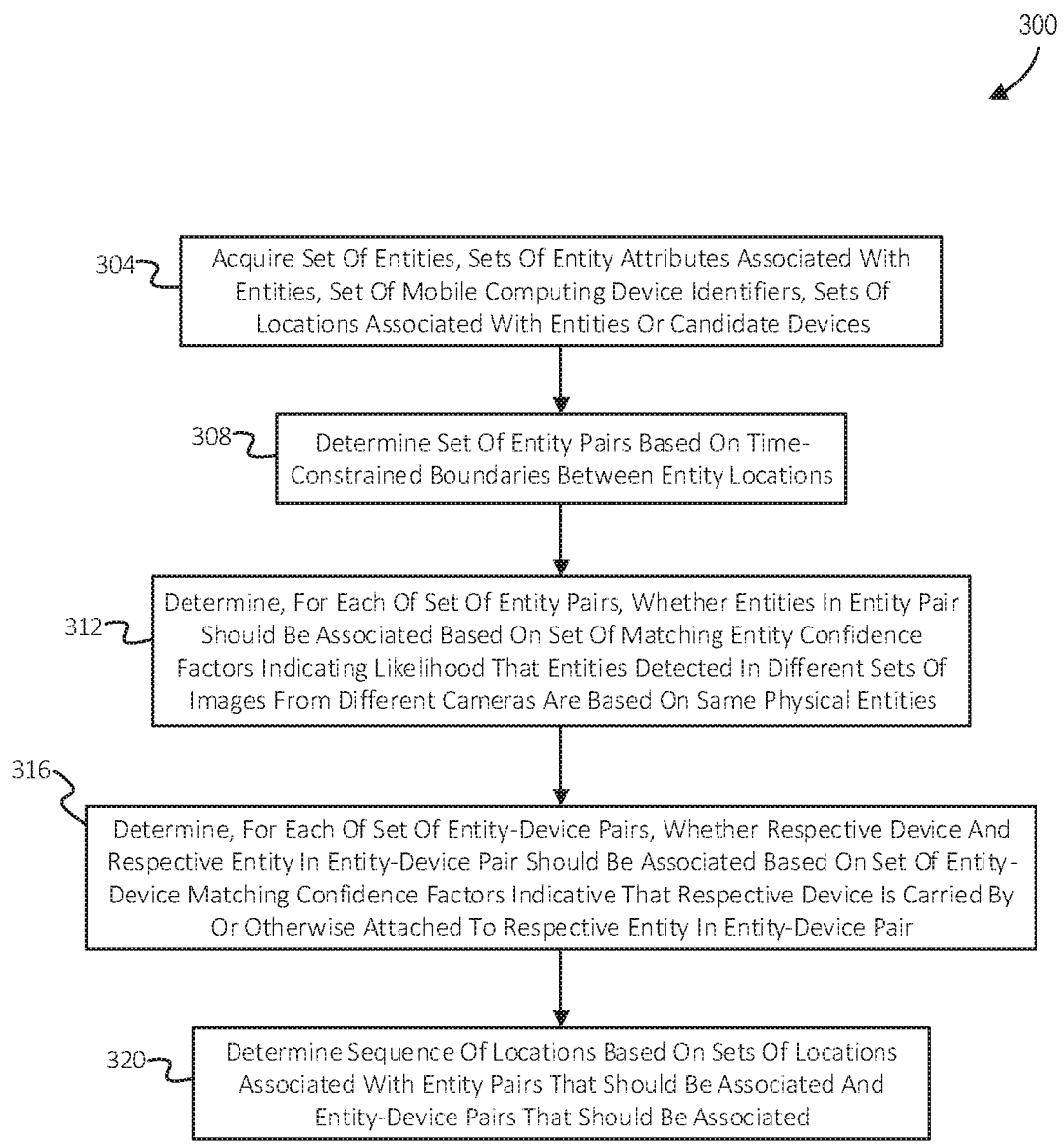
FIG. 3 is a flowchart of operations to determine associations between devices and entities, in accordance with some embodiments.

FIG. 2 and FIG. 3 are flowcharts of operations to use sensor measurements associated with a plurality of input channels to determine a sequence of locations associated with an entity, in accordance with some embodiments. In some embodiments, the process 200 and process 300, like the other processes and functionality described herein, may be implemented by an entity-tracking system that includes computer code stored on a tangible, non-transitory, machine-readable medium, such that when instructions of the code are executed by one or more processors, the described functionality may be effectuated. Instructions may be distributed on multiple physical instances of memory, e.g., in different computing devices, or in a single device or a single physical instance of memory, all consistent with use of the singular term "medium." In some embodiments, the operations may be executed in a different order from that described. For example, while the process 200 is described as performing the operations of a first set of blocks 204, 208, and 212 before performing the operations of a second set of blocks 220 and 224, the operations of the second set of blocks may be performed before the operations of the first set of blocks. In some operations may be executed multiple times per instance of the process's execution, some operations may be omitted, additional operations may be added, some operations may be executed concurrently and other operations may be executed serially, none of which is to suggest that any other feature described herein is not also amenable to variation.

FIG. 2 is a flowchart of operations to determine a sequence of locations based on a set of images and sensor measurements, in accordance with some embodiments. In some embodiments, the process 200 includes acquiring a set of images from a plurality of cameras directed to different fields of view of a monitored environment, as indicated by block 204. As used herein, an image may include a mapping of a set of values to a corresponding set of spatial positions, and may represent a color image, black and white image, structured illumination, thermal image, infrared image, x-ray image, ultraviolet image, some combination thereof, or the like. A set of images may include a single image, a plurality of images, a video, a graphical rendering of data collected by a camera, or the like. In some embodiments, the process 200 may occur concurrently while the set of cameras are used to acquire the set of images. Alternatively, or in addition, the process 200 may occur based on a set of images acquired by cameras before the process 200 begins. For example, one or more operations of the process 200 may occur based on images or sensor measurements stored on a server such as the on-premise server 180.

In some embodiments, the process 200 includes detecting a set of entities moving through a monitored environment based on the set of images, as indicated by block 208. The entity-tracking system may apply various image analysis operations and image processing operations to detect and localize the set of entities based on the set of images. In some embodiments, the system may use object recognition methods on a set of images to detect one or more entities. Object tracking methods may include detection-based tracking methods, detection-free tracking methods, single object tracking methods, multi-object tracking methods. Some embodiments may use tracking approaches may include use of a Viola-Jones object detection framework, scale-invariant feature transform (SIFT), histogram of oriented gradients (HOG), deformable parts model (DPM), or the like.

Some embodiments may use a neural network to detect an entity. As described herein, the entity-tracking system may use a neural network multiple times, where subsequent uses of the neural network may use different weights/biases/parameters from previous uses of the neural network. In some embodiments, a program being executed by the entity-tracking system may first receive a signal indicating that a new set of images have been acquired. The program may load the an image of the new set of images as an input into a neural network, where the neural network may be represented as a set of layers, where each layer made up nodes, and where each node may include a set of node values such as weights, input function values, activation function values, and biases. Each node may take an input and provide an output based on its node values. Loading the image to the neural network may include sending image data such as pixel color, pixel brightness, or the like as input values to one or more nodes. Each node may then first apply a weight to the input values, process the weighted input with one or more input functions, and apply one or more activation functions to determine an output value. These output values may themselves be used as inputs for subsequent node layers, until a final output is provided, where the final output may be interpreted as a numeric value, a category, or some other value. In addition, the loaded image be used to train the neural network during a learning operation, where the internal values of the nodes may change to match a learning target (e.g. a detected entity, an entity attribute, a position, or the like). Various types of neural networks may be used, as further described below.

In some embodiments, the neural network may include convolutional neural network such as "GOTURN," where a convolutional neural network may acquire an image as input and determine a cross-correlation based on the image to detect one or more entities or other objects in the image. Use of a neural network that includes a convolutional layer or set of convolutional operations may provide translation invariance, which may provide advantages when detecting and localizing entities based on images of moving physical entities. In addition, some embodiments may use augmented-reality (AR) development kits to recognize pre-built or custom-build entities. For example, some embodiments may include the use of various development kits such as Apple ARKit™, ARToolKit™, and Google ARCore™, to detect an entity or, as further described below, detect attributes of the entity.

In some embodiments, a convolutional neural network or its outputs may be modified or otherwise used as a part of another neural network. For example, some embodiments may use a neural network such as a recurrent convolutional neural network, a recurrent you-only-look-once (YOLO) neural network, a single shot multibox detection (SSD) neural network, or the like. Some embodiments may use a YOLO neural network, where the entity-tracking system may segment an image into a set of grid cells and then, for each respective grid cell, use a convolution operation to determine a bounding box associated with the respective grid cell. The entity-tracking system may then detect the entity based on the bounding box.

In some embodiments, the entity-tracking system may use a SSD neural network, where the entity-tracking system may determine a set of visual features in an image and a set of visual feature positions associated with the set of visual features, where the set of visual features may be determined using a convolutional neural network, other neural network, or feature detection algorithm. Using the SSD neural network may include generating a set of bounding boxes using convolution operation for each of the set of visual features, where each of the set of bounding boxes encloses one of the set of visual feature positions. For each respective bounding box in the set of bounding boxes, some embodiments may determine respective class scores using convolution operations, where the class scores are indicative of likelihoods that the bounding box is bounding an object of the object type associated with the class score, and where the object type may be found in a set of object types used to train the SSD neural network. For example, a greatest class score from a set of class scores associated with a bounding box may correspond to an object set as an entity, which may result in the area of the bounding box may be detected as including an entity.

As discussed above, in some embodiments, a camera or other sensor of the entity-tracking system may take a processor and memory storage to execute program code. In some embodiments, these sensors may be used to train and use neural networks, where the neural networks may be modified for use in reduced-power contexts. For example, in some embodiments, with reference to FIG. 1 above, the first camera 102 and second camera 103 may include processors and memory to detect and localize entities using a neural network architecture such as MobileNetV2, as described by in "MobileNetV2: Inverted Residuals and Linear Bottlenecks" [Sandler, M., Howard, A., Zhu, M., Zhmoginov, A. and Chen, L. C., 2018. *Proceedings of the IEEE Conference on Computer Vision and Pattern Recognition* (pp. 4510-4520)], herein incorporated by reference. For example, some embodiments may use depthwise separable convolutions on inputs and a set of linear bottleneck layers between convolutional blocks to detect and localize entities in a set of images.

In some embodiments, the process 200 includes determining a first set of locations based on the set of images, as indicated by block 212. In some embodiments, the process 200 may determine a location as a region of the monitored environment corresponding to a camera's field of view. For example, a first camera that has an associated first field of view may acquire an image that is used by an entity-tracking system to detect a first entity in the first field of view at a first measurement time during which an image is acquired ("image acquisition time"), where a location of the first entity may be determined include the first field of view at the first image acquisition time. In some embodiments, this location may include an overlap region of multiple fields of view.

In some embodiments, the first entity may detect locations using one or more computer vision methods based on a pixel position of the detected entity, where computer vision methods may include the implementation of various perspective transformation algorithms, homography methods, pose estimation algorithms, or the like. For example, a first camera may use a set of perspective transformation algorithms to determine a distance from a point on the surface of a monitored environment to the first camera, where the set of perspective transform algorithms may be calibrated using a set of marked locations in the monitored environment and their corresponding set of known distances in the field of view of the first camera. In some embodiments, an entity on the surface may be first processed using a homography algorithm, such as a homography algorithm that implements a three-dimensional plane-to-plane algorithm to re-project the dimensions of a detected entity or a boundary box of the detected entity based on a known angle of the first camera with respect to a surface of the monitored environment to more accurately determine entity dimensions or an entity location.

Various other tracking algorithms may be used to determine locations. For example, some embodiments may use a target tracking method comprising a Kalman Filter or a Long Short Term Memory (LSTM) network, as described in the publication, "Target Tracking with Kalman Filtering, KNN and LSTMs" [D. Iter, J. Kuck, P. Zhuang. *C. M Learning*. 2016], herein incorporated by reference. For example, the set of locations may be determined as a sequence of locations using a Kalman filter by tracking the motion of bounding boxes, such as those described above in block 208. Furthermore, in some embodiments, a Kalman filter or neural network may also be used to determine a sequence of locations as described further below at block 232.

In some embodiments, the process 200 includes determining a set of entities attributes associated with the set of entities based on the set of images, as indicated by block 216. In some embodiments, the object recognition methods described above may be used to detect and determine entity attributes, where an entity attribute may be any observable characteristic of an entity. As described above, example object recognition methods may include use of a convolutional neural network, recurrent neural network, recurrent YOLO neural network, SSD neural network or the like. For example, a height of the entity may be determined based on a bounding box after applying a 3D plane to plane operation to the bounding box of the detected entity. Alternatively, or in addition, physical features of a physical entity represented in the set of images may be detected and used to set an attribute. For example, an entity-tracking system may use a trained convolutional neural network to analyze a subset of pixels and detect the presence of black hair on a first entity. In response, the entity-tracking system may update the set of attributes for the first entity to include an indicator that the entity possesses hair or an indicator that the entity's hair color is black.

In some embodiments, the set of entity attributes may include physical attributes, such as the presence or lack of an entity feature, the shape of an entity feature, type of an entity feature, the color of an entity feature, an activity associated with the entity, or the like. An entity feature may include various physically observable components attached to an entity, such as height, sex, hair presence, hair color, clothing presence, clothing color, sex, limbs, head shape, a skin color, or the like. For example, a set of entity attribute may include a skin color, hair color, shirt type, pants type, and sex. As used herein, an attribute may include an attribute type and an attribute value, where an attribute difference may include a difference between attribute values.

In some embodiments, an attribute may include an activity attribute, where an activity attribute may include activities specific to individual entities, such as a facial expression attribute, nervous tic, or a gait attribute. In some embodiments, a gait attribute may be based on a measured gait behavior of an entity. Alternatively, or in addition, the motion of a mobile device carried by the entity as determined based on measurements made by EES can be used to determine one or more gait attributes. A gait attribute may include a set of quantities corresponding with various gait metrics such as a movement speed, postural sway, stride frequency, gait symmetry, gait dynamic range, gait characteristic curve, or the like. In some embodiments, the gait attribute may be determined using a motion sensing algorithm to analyze the set of images.

In some embodiments, an activity attribute may be associated with various other motions or poses of the human body that may be detected using custom-built or pre-built packages. For example, activities such as sitting, running, checking mobile computing devices, or the like may be detected and used to set an attribute value using trackable points on a human body, where a trackable point may be associated with a visual feature that is tracked over time. Some embodiments may include the use of various development kits such as Apple ARKit™, ARToolKit™, and Google ARCore™, to detect and categorize activity attributes, similar to the methods described above to detect entities or determine entity locations.

Some embodiments may include architecture or techniques to mitigate data sparseness issues when detecting and localizing entities, where the data sparseness issues may result from the wide variation in people or other physical entities that the entity-tracking system may be tasked to detect, localize, and reconcile with other entities. Some embodiments may use a neural networks adaptable for sparse training. For example, some embodiments may use a siamese neural network to determine attributes of an entity, where a siamese neural network may include elements of the siamese architecture described in "Learning A Similarity Metric Discriminatively, With Application to Face Verification" [Chopra, S., Hadsell, R. and LeCun, Y., 2005, June. *CVPR* (1) (pp. 539-546).], herein incorporated by reference. In some embodiments, a siamese neural network designed to determine whether a first entity is the same as a second entity may be trained using a first image comprising a portion of a first entity, where training may include using a triplet loss method. When training the siamese neural network using the triplet loss method, some embodiments may compare a baseline vector to a positive vector which may be based on the first image to regularize learning and a negative vector which is not based on the first image to force learning in the siamese neural network. As further described below in the process 300, the siamese neural network may also be used to associate different entities by comparing them to each other or to a reference model. By using a siamese neural network with triplet loss training, data sparseness issues may be reduced or mitigated.

Some embodiments may use a capsule neural network to determine an attribute of an entity, where the capsule neural network may be similar to that described in "Dynamic Routing Between Capsules," [Sabour, S., Frosst, N. and Hinton, G. E., 2017. *Advances In Neural Information Processing Systems* (pp. 3856-3866)], herein incorporated by reference. For example, some embodiments may learn a global linear manifold between an entity and its poses using a weights matrix, allowing for an entity-tracking system to detect an entity independent of its pose and likewise also categorize a pose of the entity. These detected poses or their associated activity labels may be included as a part of the attributes of an entity. As further described below in the process 300, the capsule neural network may also be used to associate different entities by comparing them to each other or to a reference model.

Some embodiments may use an attention-based neural network to determine an attribute, where an attention-based neural network may be similar to the attention-based neural network described in "Attention-based temporal weighted convolutional neural network for action recognition," [Zang, J., Wang, L., Liu, Z., Zhang, Q., Hua, G. and Zheng, N., 2018, May. *IFIP International Conference on Artificial Intelligence Applications and Innovations* (pp. 97-108). Springer, Cham.], herein incorporated by reference. For example, the attention-based neural network may use a transformer to encode and decode a set of attention weights to the set of images to determine and modify the order and importance of training data and input data, where an attention weight indicates an amount of relevance to the neural network. In some embodiments, the attention weight may be increased in response to the detection of an attribute. As further described below in the process 300, the attention-based neural network may also be used to associate different entities by comparing them to each other or to a reference model.

In some embodiments, one or more of the set of entities attributes or associated set of entity locations may have a set of associated measurement confidence values. Each measurement confidence value associated with an attribute or entity location may be the same as or different from other measurement confidence values. In some embodiments, different attribute values of a same record in a dataset may have correspondingly different types of measurement confidence values. For example, for a first entity associated with a first record associated with a first image captured by a camera, the computed entity position of the first entity may have a first measurement confidence value equal to 1 meter, the computed entity attribute corresponding with a shirt color may have a second measurement confidence value equal to 20 color units in the 24-bit RGB color scheme, and the predicted identity of the first entity may have a third measurement confidence value equal to 95%. The measurement confidence values may be correlated or based on various types of measures of dispersion. For example, an entity attribute comprising a first label of "[201, 99, 119]" representing the color "navy blue" may have an associated measurement confidence value of "20" to indicate that the 90% confidence interval for the entity attribute being within 20 units of the in the 24-bit RGB color scheme. As further discussed below, some embodiments may have attributes or other measured values that have a 100% measurement confidence value. For example, a measured MAC address of a mobile computing device (e.g., cell phone) or an associated measurement time may have an associated measurement confidence value of 100%.

In some embodiments, the process 200 may include acquiring a set of sensor measurements from a set of sensors, where the set of sensor measurements is different from the set of images, and where the set of sensors is different from the set of cameras, as indicated by block 220. In some embodiment, as described above, the set of sensors may include a set of EES to track a mobile computing device via the device's emitted wireless signals as it moves through a monitored environment. The measurements made by the set of EES from the wireless signals may include signal parameters such as RSSI, signal frequency, data transmitted in the signals, or the like. For example, an EES may send a set of RSSI values, a set of device identifiers associated with the RSSI values, and a set of timestamps associated with the measurement time for each of the set of RSSI values to a server such as the on-premise server 180. Alternatively, or in addition, a server or other computing device receiving signals from an EES may assign a timestamp to the sensor measurement, where either the time assigned by the EES or the time assigned by the signal-receiving computing device may be an EES.

In some embodiments, an EES may determine the existence of a mobile computing device based on WLAN probe requests. For example, the EES may acquire WLAN probe requests and WLAN association requests and transmit either or both signal properties and data transmitted in the signal to a server, such as an on-premise server or to a cloud computing system. Furthermore, in some embodiments, a mobile computing device may request access to WLAN infrastructure via an EES. In response, the EES may send the mobile computing device an association request that includes a formatted protocol data unit (i.e. a management frame in the preceding scanning and authentication phases) to the mobile computing device using information supplied by the mobile computing device or other signal values (e.g. RSSI). The entity-tracking system may then use the response to the association request to assign an identifier to the mobile computing device.

In some embodiments, the entity-tracking system may protect an entity identity using various methods, such as a method using visitor correlation groups (VCGs). For example, the EES may be used as the proximity recognition devices described by U.S. Pat. No. 9,590,950, herein incorporated by reference. In some embodiments, a VCG may include a set of EES associated with a shared region of a monitored environment, where the use of salting and hashing may result in a plurality of VCGs in one shared monitored environment.

In some embodiments, the entity-tracking system may assign an identifier to a mobile computing device based on an identifier provided by the mobile computing device itself. For example, if a mobile computing device provides a MAC address "00:0A:00:00:0A:A0," the entity-tracking system may assign the identifier device identifier to be identical to "00:0A:00:00:0A:A0." Alternatively, or in addition, some embodiments may include operations to assign identifiers to mobile computing devices that do provide unique identifiers. For example, the entity-tracking system may derandomize or otherwise assign identifiers to devices emitting wireless signals containing randomized MAC addresses. In some embodiments, the entity-tracking system may implement one or more operations to assign identifiers to devices emitting randomized MAC addresses. For example, some embodiments may determine false device identifiers in a set of device identifiers and eliminating the false device identifiers and use the accurate unique device identifiers to identify corresponding mobile devices associated with each accurate unique device identifications, as described in U.S. Pat. No. 9,998,907, herein incorporated by reference. In some embodiments, the entity-tracking system may assign new unique identifiers to the devices associated with false unique identifiers.

In some embodiments, an entity-tracking system may include a set of ultrasonic sound sensors to acquire sound measurements of sounds emitted by an entity as the entity move through a monitored environment. The sounds may be used determine one or more attributes of the entity. For example, the sensor measurement from a set of ultrasonic sound sensors may be used to detect a set of heartbeats.

Furthermore, as described below, matching entity attributes may include matching sound measurements.

In some embodiments, an entity-tracking system may include a set of temperature sensors to measure entity temperatures of an entity as the entity move through a monitored environment, where a temperature sensor may include a thermal imaging sensor such as a thermographic sensor. For example, some embodiments may include a thermal IR camera acting as a thermal infrared sensor to determine temperature of an entity based on the amount of IR radiation emitted by the entity. In some embodiments, a temperature of an entity may be used to determine one or more attributes of the entity. For example, the temperature measurement from a set of temperature sensors may be used to determine the skin temperature of an entity. Furthermore, as described below, matching entity attributes may include matching temperature measurements.

In some embodiments, an entity-tracking system may include a set of chemical sensors to measure a identifying set of volatile chemicals ("volatile chemical signature") being emitted or other diffusing from an entity (i.e. "scent"). The scent may be used determine one or more attributes of the entity. For example, the scent measurements from a set of chemical sensors may be used to detect a volatile chemicals signature indicative of a specific entity and be used to track the specific entity in a monitored environment. Furthermore, as described below, matching entity attributes may include matching scent measurements.

In some embodiments, the process 200 may include determining a second set of locations based on the set of sensor measurements, as indicated by block 224. The second set of locations may include or be otherwise associated with device positions determined from computations based on the set of sensor measurements. In some embodiments, a physical position may be determined using measurements acquired from a set of EES and a set of known coordinates of the EES. In some embodiments, the known coordinates of the EES may include X, Y, and Z cartesian coordinates of each EES in a set of EES, which may be stored in a database that is part of or in communication with the entity-tracking system. Alternatively, or in addition, the coordinates of each EES may be stored within EES and communicated to the entity-tracking system. The coordinates of an EES may be determined and stored during the initial installation and configuration of the monitoring system.

The entity-tracking system may determine a device position using methods such as lateration, angle of arrival (AoA), and/or time of flight (ToF) methods. A lateration method may include a multilateration method, wherein multiple measurements are combined with a propagation model to determine distances between a wireless signal source and the EES to then determine a physical position of a device emitting the wireless signal. An AoA method can be based on the multiple antennas used for Multiple Input Multiple Output (MIMO) interfaces, wherein the method can include estimating an AoA of multipath signals received at the antenna arrays in the EES and applying triangulation to calculate the location of devices emitting probe requests. A ToF method can include using a timestamp provided by the EES to calculate a ToF of probe requests and then use this information to determine a distance and relative position of a device emitting the probe request with respect to one or more EES. Furthermore, an EES may include multiple antennas may be tuned to a same band and determine an angle of arrival of multipath signals received at the multiple antenna. In some embodiments, other signal parameters, such as a phase shift, a spectral distribution, or the like may be used in addition to or as an alternative to using an amplitude for the purpose of triangulating a physical position.

In some embodiments, the entity-tracking system may compare a set of measurements such as RSSI or other signal parameters correlated with a wireless signal strength from the set of EES, where each of the set of measurements may have an associated measurement time. The entity-tracking system may then compare RSSIs to determine a nearest EES associated with the greatest RSSI to determine a device's location within the monitored environment, where the location may be the range of in which the nearest EES would be able to provide the greatest RSSI. The location of a mobile computing device may bound by the non-overlapping sensing ranges of an EES. For example, if a mobile computing device is at a wall of a monitored space, and if a wireless signal from the mobile computing device is detectable by only a first EES and not measurable by a second or third EES, the position of the mobile computing device may be predicted based on the area of the first EES that may sense devices which are not overlapped by the second EES or third EES, and may determine that the mobile computing device is near the wall. Such a method may be used for determining a mobile computing device location using only one EES instead of a plurality of EES.

In some embodiments, the entity-tracking system may include instructions to analyze one or more historical signal parameters such as historical RSSI values in order to improve triangulation accuracy. For example, a historical maximum signal amplitude may be determined after a predetermined number of measurements are acquired from an EES. The maximum amplitude may be correlated to a distance between a mobile computing device and the corresponding EES which detected the maxima based upon a calculated position. In subsequent measurements of the mobile computing device, the correlation may be used to provide an estimated position of the mobile computing device. For example, if the RSSI of a first signal of a first device is −60 dBm and is determined to result from the first device when it is 4 meters away from the measuring EES, a subsequent measurement using the EES of a second signal of the first device that results in a RSSI value equal to −60 dBm may be associated with a distance of 4 meters.

In some embodiments, the process 200 may include determining a sequence of locations based on associated sets of locations, as indicated by block 232. As discussed further below in the description for the process 300, the associations may be based on a set of entity attributes. In some embodiments, a first set of locations may be associated with a second set of locations if their corresponding entities are associated. For example, a first set of locations of a first entity may be associated with a second set of locations of a second entity if the first entity and second entity are associated based on a confidence factor indicative of the first entity being based on the same physical entity as the second entity. Similarly, a first set of locations of a first entity may be associated with a second set of locations of a mobile computing device if the first entity is associated with the mobile computing device. As discussed in the process 300 further below, various methods may be used to determine which entities should be associated with each other or which devices should be associated with which entities based on one or more calculated confidence factors, where the confidence factors may be determined based on entity attributes such as detected physical attributes, entity positions, or the like.

Once the associations are determined, some embodiments may determine a sequence of locations based on one or more of the sets of associated locations and their associated measurement times. In some embodiments, the sequence of locations can be computed using a multivariate interpolation method. Implementing a multivariate interpolation method may include implementing any one of a set of possible methods usable to determine a sequence of locations based on a potentially noisy set of known locations. Some embodiments may use a Kalman filter, as discussed above, to determine a sequence of locations based on the set of locations that are determined based on the set of images and the set of locations that are determined based on EES sensor measurements. For example, some embodiments may build an initial state based on a set of positions and a covariance between a velocity and position of the entity, where the initial state may include an initial position and velocity. The initial state may be represented by a linear stochastic equation with a prediction matrix associated with the initial state, a control matrix associated with a control vector that may be equal to zero, and an uncertainty function. For each update step, the entity-tracking system may implement a first stage that includes determine a predicted position and velocity based on the prediction matrix, uncertainty function value, and previous state, where the first stage also may also include determining a predicted covariance. The entity-tracking system may then implement second stage that includes determining a gain based on the predicted covariance, determining a new position value based on the gain, and update the covariance value based on the new position. Alternatively, or in addition, the sequence of locations may be determined using a neural network to predict a sequence of locations based on one or more sets of locations determined from sensor measurements such as a set of images or a set of entity temperatures.

Alternatively, or in addition, some embodiments may use delaunay triangulation, bicubic interpolation, Barnes interpolation, Bezier surface interpolation, bilinear interpolation, Lanczos resampling, or the like. In some embodiments, implementing the multivariate interpolation may include implementing a two-dimensional interpolation method instead of a higher-dimensional interpolation method to reduce computation time. Additionally, or alternatively, some embodiments may implement a Wiener-Kolmogorov filter, nearest neighbor interpolation method, gaussian process regression, inverse distance weighting, natural neighbor interpolation, spline interpolation, radial basis function interpolation, or the like.

In some embodiments, the set of locations associated with an entity having the least amount of uncertainty may be used to determine the sequence of locations, where the uncertainty may be correlated with the uncertainty radius from a predicted position. For example, if a first set of locations associated with an entity has an average radius of certainty equal to one meter and a second set of locations associated with an entity has an average radius of certainty equal to three meters, the entity-tracking system may be use only the first set of locations to determine an sequence of locations for an entity. Alternatively, or in addition, a plurality of sets of locations associated with different devices or sets of locations determined based on a set of images may be used to determine a sequence of locations. For example, an entity-tracking system may use a first set of locations determined based on wireless signals emitted by a first device and a second set of locations determined based on wireless signals emitted by a second device, where both devices are determined to be attached or otherwise associated with an entity during entity motion. In some embodiments, the location of an entity as determined from a set of images may be used to verify that a determined sequence of locations is within each of the set of image-determined locations at their corresponding measurement times.

In some embodiments, the location of an entity determined from a video or other set of images may be used to determine a sequence of locations, either with or without locations determined based on wireless signals from electronic devices being carried by the entity or other locations determined using various other input channels associated with different types of sensors. Various other sets of locations that may be determined from other channels may be used to determine the sequence of locations, such as a set of locations from temperature sensors, chemicals sensors, sound sensors, or the like. For example, the entity-tracking system may determine a sequence of locations from a first set of locations determined using ultrasound sensors that measured entity heartrates or entity footsteps and a second set of locations determined using chemical sensors that measured the volatile chemical signatures emitted by entities. The determination of the sequence of locations may be performed for some or all of the detected entities in a monitored environment and may be performed at a pre-determined frequency.

In some embodiments, the frequency with which sensor measurements are updated or with which the sequence of locations are determined may be greater than once every 1 second, greater than once every 5 seconds, greater than once every 10 seconds, greater than once every minute, greater than once every five minutes, or the like. In some embodiments, the entity-tracking system may update the sequence of locations over a pre-determined duration of time every day, such as during a specific 30-minute interval every day. Alternatively, or in addition, an entity-tracking device may detect entities, determine sets of locations or perform any of the other operations described above in response to an event or a request.

In some embodiments, the process 200 may include determining a characterization record for one or more of the set of entities and storing the characterization record in a memory storage, as indicated by block 236. In some embodiments, a characterization record of the entity may include an entity identifier, entity attributes, one or more sets of locations associated with the entity, sensor measurements associated with the entity, one or more calculated sequences of locations associated with the entity, other information about the entity, or the like. For example, the characterization record of an entity may include a set of images that depict the entity, signal parameters associated with a mobile computing device being carried by the entity, entity data sent by the mobile computing device, physical attributes of the entity, temporal data, or the like. The set of images may include one or more captured still image or captured video footage. The mobile communication device data may include a Wi-Fi identifier, a MAC identifier, a Bluetooth identifier, a cellular identifier, a near field communication (NFC) identifier, and a radio frequency identifier or any other identifier associated with the mobile computing device. The temporal data may include a time at which corresponding video data of the entity is captured or a time at which corresponding wireless signals are acquired. The memory storage in which the record is stored may be a memory storage attached to a sensor such as a camera, a memory storage attached to an on-premise server, a memory storage of a cloud computing system, or the like.

In some embodiments, the characterization record may include values indicating an entity name or an entity residential address, a date of birth, other personal information, or the like. For example, a system may also acquire information about an entity based on data available using a data mining subsystem (DMS). The DMS may acquire entity data from a third party about an entity and associate the entity data with data acquired from social media accounts, registration information, or the like. For example, the DMS may acquire entity identity information associated with an entity based on information acquired from a conference registration form and use the entity identity information to determine a full name, address, or other information about the entity. Furthermore, in some embodiments, an entity-tracking system may update or add attributes to an entity after matching a detected entity with a previously-detected entity from a previous visit. For example, an entity-tracking system may determine a number of visits or frequency of visits to a monitored environment of the person to the monitored environment. In some embodiments, the entity-tracking system may compare data obtained from a first source (e.g., a non-government database, a government database, and one or more previously-generated characterization records) to a detected entity to identify an entity based on the data from the first source.

In some embodiments, the process 200 may include displaying the set of entities on a graphical display device, as indicated by block 250. The system may display a graphical representation of the set of entities on one or more graphical display devices such as a computer screen or tablet. A graphical representation of the monitored environment may include a two-dimensional rendering, a three-dimensional rendering, a set of superimposed photographic images, streaming video feeds that include entities, or the like. In some embodiments, the graphical representation of the monitored environment may be displayed concurrently with the set of entities or indicated locations of importance. For example, the visual representation of the monitored environment can show the locations of detected entities and safety resources in the monitored environment. Safety resources may include defibrillators, fire extinguishers, emergency phones, exit egresses, or the like.

In some embodiment, a monitored environment may be segmented into sectors, where each respective sector may be displayed on different screens. Alternatively, or in addition, multiple sectors may be displayed on a single screen. In some embodiments, the entity-tracking system may, for a particular sector, display expanded information for entities representing people in that particular sector or entities expected to arrive in that particular sector. In some embodiments, the entity-tracking system may dynamically show sectors individually or concurrently with other sectors on a same screen based on a detected activity level or detected activity type. For example, an entity-tracking system may display a field of view corresponding to a first sector on a screen by itself if a number of entities moving in the field view are greater than three, or otherwise display the field of view corresponding to the first sector with other fields of view. In some embodiments, the entity-tracking system may allow manual or automated selection of different sectors for display and may include one or more incident detection routines to detect triggering activities and display an image or video from the camera capturing the triggering activity. By dynamically re-allocating screen space to display images or videos of a monitored environment, the entity-tracking system increases the flexibility of observers of the monitoring environment to notice unexpected changes in the monitored environment and adapt their responses to the unexpected changes.

For example, the system can determine the location of individuals of interest within the set of entities. In some embodiments, information obtained from timeline matching (further described below) may be presented on the graphical display device. In addition, information in a characterization record associated with one or more of the displayed entities may be presented on the graphical display device. For example, after matching a first entity to an entity name, the graphical display device may include the entity name in proximity to a graphical representation of the first entity. In some embodiments, the system may update the graphical display device of the monitored environment in real-time, wherein updating the graphical display device of the monitored environment in real-time includes a delay of no greater than 10 seconds between when an event occurs (e.g. an entity moves, an entity performs an action) and when the event is displayed on the graphical display device. Alternatively, or in addition, the system may display historical tracking of entity movement through a monitored environment.

In some embodiments, the entity-tracking system may change or be controlled to change an amount, type, or granularity of information presented in a graphical display device. For example, the system may include a graphical interface that includes a filtering button or filtering text box to select or otherwise filter data types based on a filter input (e.g. a view toggle). For example, in some embodiments, the view of a graphical display device may include an input filter such as "Identified Individuals," "Anticipated Behaviors," or "Identification Status of Individuals," where an input filter of "Identified Individuals" may result in the entity-tracking system displaying icons of entities associated with identified individuals presented against a backdrop of a map of the monitored environment on the graphical display device. Alternatively, or in addition, a filter input may include a set of data layers, where selection of each of the set of data layers controls an amount of information for display. For example, selection of a first data layer may result in the display of only an identification and status, and selection of a second data layer may result in the display of the identification, status, and monitoring context (e.g. a security clearance label, whether the entity is a high-value customer, or the like).

For example, in response to receiving the filter input to only display information about entities detected to have entered a first field of view between 3:00 PM and 3:05 PM, the system may first, using the methods described above, identify a first set of entities based on their attributes and signals emitted by their personal mobile computing devices, and track the first set of entities over time as they move through a monitored environment. The graphical display device may then show only the first set of entities or otherwise highlight the first set of entities in contrast to other entities shown in the graphical display device. In some embodiments, specific portions of a monitored environment may be sent to different graphical display devices, which may increase granularity and control of monitoring operations. In addition, some embodiments may display an identifier and other information about an entity in response to a user placing a cursor over an icon representing the entity. In some embodiments, display of entities may be changed based on a degree of confidence in an identification. For example, some entity-tracking systems may display entities for which a confidence factor is more than 95% certain as a first color and otherwise display the entities as a second color. In some embodiments, this type of information might be presented in a display screen, where display of this information in a display screen may allow for the determination of how many of the individuals are characterized and whether one or a group of unknown individuals have entered the environment.

In some embodiments, the entity-tracking system may detect an unexpected event and perform warning actions. For example, an entity-tracking system may detect that an entity has entered a restricted area. In response, the system may display a warning, send a warning message to a mobile computing device, send a warning message to a graphical display device for display, or otherwise generate an indicator of the unauthorized entry. In some embodiments, the entity-tracking system may send a warning message to a mobile computing device if an entity enters a restricted area of the monitored environment. For example, if an individual enters a restricted area of the monitored environment, the entity-tracking system may detect that the individual has entered the restricted area based on sensor measurements and images using the methods described above. In some embodiments, the restricted area may be universally restricted to entities not being an entity of a specific type. For example, a restricted area may be restricted to all entities not carrying a security fob. Alternatively, or in addition, a restricted area may be restricted to a specific entity or entity type. For example, the entirety of a monitored environment may be deemed to be a restricted area to a previously-identified thief.

In some embodiments, the entity-tracking system may send a warning message to a mobile computing device if an entity leaves a permitted area of the monitored environment. For example, if an entity is expected to be within a permitted area of the monitored environment and not leave the permitted area for a duration of time, the entity-tracking system may detect that the entity has left the permitted area based on sensor measurements and images using the methods described above. In some embodiments, a permitted area may be permitted for a specific entity or entity type. For example, a specific room of a monitored environment may be deemed to be a permitted area for a set of entities having the "toddler" attribute, where a "toddler" attribute may be set based on a detected entity height being below a height threshold. An entity-tracking system may send a warning message to a mobile computing device if an entity having the "toddler" attribute leaves the permitted area and not send the warning message if an entity not having the "toddler" attribute leaves the permitted area.

In some embodiments, the entity-tracking system may detect an event and effect a physical change in response to the event. In some embodiments, the entity-tracking system may use one or more neural networks to detect an event. For example, the entity-tracking system may use a LSTM to detect the occurrence of a fire based on measurements from a set of cameras and a set of temperature sensors. The physical change may be a change in power flow to an area, activation of a gate closure mechanism, activation of a fire suppression system, an unlocking of a door, turning on of a light, or the like. For example, an entity-tracking system may increase the intensity of lighting in an area of the monitored environment in response to the detection of activities categorized as "suspicious" by a neural network of the entity-tracking system.

FIG. 3 is a flowchart of operations to determine associations between devices and entities, in accordance with some embodiments. Operations of the process 300 may begin at block 304. In some embodiments, the process 300 includes acquiring a set of entities, sets of entity attributes associated with entities, a set of mobile computing device identifiers, and sets of locations associated with entities or candidate devices, as indicated by block 304. In some embodiments, the set of entities, sets of entity attributes associated with entities, set of mobile computing device identifiers, and sets of locations associated with entities or candidate devices may be determined using operations similar to or identical to those described above in the process 200. For example, people captured in the video feeds acquired by a first camera directed to the field of view ICS1 of the first camera can be detected as entities as described in the description for block 204, entity positions may be captured as locations as described in the description for block 208, and physical features of these people can be captured as attributes as described in the description for block 212, where labels and values for these entities, entity positions, and attributes may be represented by Table 1. Similarly, people captured in the video feeds associated with a field of view ICS2 of a second camera can be detected as entities, and physical features of these people can be captured as attributes, where labels and values for these entities and attributes may be represented by Table 2. As shown in Table 1 and Table 2, "Att1: Sex," "Att2: Hair Color," "Att3: Footwear," and "Att4: Height" may represent attributes of entities, where the attributes may include a predicted entity sex, entity hair color, entity footwear color, and entity height, respectively:

TABLE 1

Entities and Entity Attributes Detected in ICS1 at 7:32 AM

| Entity | Measurement Time | Entity Position | Att1: Sex | Att2: Hair Color | Att3: Footwear | Att4: Height |
|---|---|---|---|---|---|---|
| Entity 2 | 7:32 AM | $(x_2, y_2, z_2)$ | F | Blond | Black | 5' 6" |
| Entity 3 | 7:32 AM | $(x_3, y_3, z_3)$ | M | Brown | Black | 5' 10" |

TABLE 2

Entities And Entity Attributes Detected in ICS2 at 7:37 AM

| Entity | Time of Measurement | Entity Position | Att1: Sex | Att2: Hair Color | Att3: Footwear | Att4: Height |
|---|---|---|---|---|---|---|
| Entity 10 | 7:37 AM | $(x_{10}, y_{10}, z_{10})$ | M | Black | Black | 5' 8" |
| Entity 11 | 7:37 AM | $(x_{11}, y_{11}, z_{11})$ | F | Brown | Black | 5' 7" |

In some embodiments, the process 300 includes determining a set of entity pairs based on time-constrained boundaries between entity locations, as indicated by block 308. In some embodiments, as described further below, multiple entities may be detected from a set of images, where the multiple entities may actually be based on a same physical entity, and may thus be associated with each other. In some embodiments, the set of possible entity pairs to search through may be reduced by implementing a spatially constrained search, where a spatially constrained search may determine time-constrained boundaries associated with entities for each respective location and measurement time associated with an entity. By reducing the set of possible entity pairs to search through, the efficiency of the operations to determine a sequence of locations for an entity may be increased.

In some embodiments, the spatially constrained search may be implemented by determining, for a respective first entity detected to be at a first location at a first measurement time, a time-constrained boundary from the first location that is based on time difference between the first measurement time and the second measurement time. In some embodiments, the boundary from the first location may be based on an estimated maximum distance from the first location that an entity could travel within the time difference. The first location may be determined based on one or more data channels. For example, the first location may be determined from a set of images. Alternatively, or in addition, the first location may be determined based on EES measurements, temperature sensor measurements, chemical sensor measurements, sound sensor measurements, or the like.

For example, with respect to Table 1 and Table 2 above, the system may perform operations to track an entity found in the location associated with the field of view ICS1 at 7:32 AM by determining whether the first entity is the same as other entities detected in the sets images of other field of views, as further described below for block 312. When searching through other detected entities, the entity-tracking system may determine that the location associated with the field of view ICS2 is within a time-constrained boundary from ICS1 and that the location associated with a field of view ICS3 is not, where the time-constrained boundary of the location associated with ICS1 can be based on the time between measurements. For example, the time-constrained boundary can be the distance from a location after walking for five minutes (e.g. 500 meters). In response to a determination that the location associated with ICS2 is within the time-constrained boundary and that the location associated with ICS3 is not within the time-constrained boundary, the system may search images and other sensor measurements associated with the location associated with ICS2 to detect a match for a first entity before searching records associated with the location associated with ICS3. Furthermore, if the location associated with ICS3 is outside of the time-constrained boundary, some embodiments may penalize a confidence factor indicative of the likelihood that the first entity detected in the location associated with ICS1 at 7:32 AM is the same as a third entity detected in the location associated with ICS3 at 7:37 AM.

In some embodiments, the process 300 includes determining, for each of the set of entity pairs, whether entities in the entity pair should be associated based on a set of matching entity confidence factors, as indicated by block 312. In some embodiments, the entity-tracking system may detect multiple entities based on a set of images and analyze attributes of the multiple entities to determine whether they are actually based on a same physical entity and should thus be associated with each other. The determination may be based on a matching entity confidence factor, where the matching entity confidence factor is indicative of the likelihood that entities detected based on different sets of images (or other sensor measurements) from different cameras (or other sensors) are based on a same physical entity. For example, a first confidence factor may be indicative of the likelihood that the first entity of a pair of entities and the second entity of the pair of entities are actually based on the same physical entity captured using different sensors.

In some embodiments, an entity-tracking system may associate a pair of entities with each other by associating both entities with a statistical reference model ("reference model") that includes attributes of the pair of entities, where the pair of entities may have been detected from a set of images from multiple cameras. In some embodiments, the entity-tracking system may compare a first set of attributes of a first entity to a second set of attributes of a second entity or reference model to determine a matching entity confidence factor. If the matching entity confidence factor is greater than a matching confidence threshold, a determination may be made that the first entity and the second entity are based on a same physical entity. In response, the entity-tracking system may determine that the two entities should be associated.

In some embodiments, the entity-tracking system may compare a set of attributes or reference model with a subsequent set of attributes using a scoring system to determine a matching entity confidence factor. In some embodiments, the entity-tracking system may set a first entity as a reference model or otherwise determine the reference model based on the first entity. The entity-tracking system may then apply the scoring system when comparing the reference model attributes to attributes associated with other entities, where equivalent or otherwise similar attributes between the first set of attributes and second set of attributes increase the matching entity confidence factor and non-matching or otherwise non-similar attributes decrease the matching entity confidence factor. The scoring system may include different criteria or operations for different attribute type.

Alternatively, or in addition, some embodiments may determine a matching entity confidence factor using a clustering algorithm. For example, some embodiments may use a density-based clustering algorithm to a set of attributes amongst the set of entities associated with the set of entity pairs in order to determine which of the set entities are most similar to each other. During the implementation of the clustering algorithm, some entity-tracking systems may be assigned different weights during feature scaling to different attributes, where certain attributes are given higher weights. For example, during feature scaling, some embodiments may set the weight for hair color attribute to significantly less than the weight associated with an arm-length to height ratio attribute to account for the possibility that camera color quality may vary greatly in a monitored environment, but a calculated arm-length to height ratio should remain consistent regardless of camera quality.

In some embodiments, an entity-tracking system may require a pair of attributes to be identical to each in order for the pair of attributes to have a positive contribution to a matching entity confidence factor. Alternatively, an entity-tracking system may allow variances between a pair of attributes to be within a tolerance threshold while still increasing the entity confidence factor, where the tolerance threshold may be based on an associated measurement confidence value. For example, if a first set of attributes may be represented by the array "[shirtColor: #0000FF, pantsColor: #FFC0CB'] and a second set of attributes may be represented by the array "[shirtColor: #0000A0, pantsColor: #FF0000]," some embodiments may determine that the color differences between the attributes are within a color tolerance threshold, where the color tolerance threshold may be determined based on the measurement confidence values for color. In response, the entity-tracking system may increase a corresponding matching entity confidence factor. In some embodiments, an entity-tracking system may determine a change in the matching entity confidence factor based on a difference value between a pair of attributes or a threshold for the attribute, where an increase in the difference value is correlated with a reduced positive change or increased negative change on the matching entity confidence factor. For example, a first set of attributes may include a set of gait attribute types and their corresponding set of gait attribute values, where the first set attributes may be represented by the array "[gaitVelocity: 110 cm/s, gaitPitch: 6.5 degrees]." In the same example, a second set of attributes may include the same set of attribute types and a different corresponding set of gait attribute values, where the second set attributes may be represented by the array "[gaitVelocity: 110 cm/s, gaitPitch: 8.9 degrees]." In this example, some embodiments may increase the matching entity confidence factor based on the values for the attribute "height" being less than a first threshold for the attribute gaitVelocity, and some embodiments may decrease the matching entity confidence factor based on the difference in gaitPitch between the two attributes values being greater than a first threshold for the attribute gaitPitch.

In some embodiments, the various individual attributes and their corresponding measurement confidence values may be combined to determine whether two entities are based on a same physical entity and should be associated with each other. For example, the measurement confidence values may be used when determining a matching entity confidence factor. For example, a matching entity confidence factor may be determined based on a dot-product of measurement confidence values. For example, if the confidence values for a first set of attributes is equal to [0.2, 0.8, 1.0] and the confidence values for a second set of attributes is equal to [0.8, 0.8, 1.0], the dot-product of the two confidence values may be equal to 1.8, since 0.16+0.64+1.0 is equal to 1.8. The dot-product may be normalized to a 0 to 1 scale, resulting in a total measurement correction value equal to 0.6. The product of the normalized total measurement correction value and an initial matching entity confidence factor may then be used to determine a matching entity confidence factor. For example, using the methods described above, an initial matching entity confidence factor may be 0.8. After multiplying the matching entity confidence factor by the total measurement correction value 0.6, the matching entity confidence factor may be equal to 0.48.

While the above discloses determining confidence factors using a dot-product, other methods may be used. For example, some embodiments may use a neural network, such as a siamese neural network, capsule neural network, attention-based neural network, or some combination thereof to determine a confidence value for determining the likelihood that two entities are based on a same physical entity. For example, a trained siamese neural network may use a first image that includes a face of a first entity captured by a first camera and a second image that includes a face of a second entity captured by a second camera as inputs to determine if the first entity and second entity are based on the same physical entity.

In some embodiments, as determinations are made that entities from different cameras are based on a same physical entity and should be associated with each other, a reference model associated with the entities may be updated. For example, if a determination is made that a first entity should be associated with a second entity from a second camera, the numerical attributes for height may be updated for the reference model based on both height values such that the tolerance for height differences are increased. As additional determinations are made if whether entities should be associated, subsequent entities may be compared to the updated reference model to determine whether detected entities should be associated with each other.

In some embodiments, upon a determination that the matching entity confidence factor satisfies the matching confidence threshold, the entity-tracking system may associate the first entity with the second entity. The entity-tracking system may associate the first entity with the second entity directly, such as by updating a record representing the second entity to include a reference to the first entity, Alternatively, or in addition, the entity-tracking system may associate the first entity with the second entity by updating a record indicating that the first entity is associated with the reference model and updating a second record indicating that the second entity is associated with the reference model. Thus, multiple entities may be associated with each other if each of the multiple entities are associated with a reference model.

In some embodiments, a determination that a first entity and a second entity should be associated may be made based on a set of confidence factors, where each of the set of confidence factors indicate a likelihood that the first entity and one of a set of candidate entities captured within a same time range of a measurement time are based on a same physical entity. For example, if a first confidence factor associated with a first pair including a first entity and a first candidate entity is 83% and a second confidence factor associated with a second pair including the first entity and a second candidate entity is 86%, the system may determine that the second pair of entities should be associated. In some embodiments, a determination that two entities are based on the same physical entity may be made based on a confidence threshold. For example, if a confidence threshold is 80%, and the greatest matching entity confidence factor associated with any entity pair is 79%, some embodiments may determine that no match was found for the first entity.

For example, using the methods above, an entity-tracking system may calculate a list of matching entity confidence factors for a set of entity pairs that includes the pair of Entity 1 with one of "Entity 11," "Entity 45," or "Entity 93." The matching entity confidence factors may based on the sets of attributes or locations associated with each of the pairs of entities. The column labeled "Field of View" represents the field of view associated with the location in which Entity 11, Entity 45, and Entity 93 may be positioned at their respective measurement time:

TABLE 3

Entities Matched with Entity 1 Over Time

| Entity | Matching Entity Confidence Factor | Field of View | Entity Position | Measurement Time |
|---|---|---|---|---|
| Entity 11 | 0.8 | ICS2 | $(X_{11}, Y_{11}, Z_{11})$ | 7:37 AM |
| Entity 45 | 0.9 | ICS8 | $(X_{45}, Y_{45}, Z_{45})$ | 7:42 AM |
| Entity 93 | 0.91 | ICS5 | $(X_{93}, Y_{93}, Z_{93})$ | 7:47 AM |

As shown in Table 3 above, if the confidence threshold is 0.9, then the entity-tracking system may determine that the entity pair that include Entity 1 and Entity 11 should not be associated because 0.8 is less than 0.9. Similarly, the entity-tracking system may determine that the entity pair that include Entity 1 and Entity 45 or the entity pair that includes Entity 1 and Entity 93 may be associated because both have corresponding matching entity confidence factors that exceed 0.9 and are within their respective time-constrained boundaries of Entity 1 and each other.

Using the methods discussed above, an entity-tracking system may track an entity as is moves through overlapping or non-overlapping fields of view between cameras. In some embodiments, the cameras or computing devices processing camera outputs may be pre-calibrated to recognize sections of the cameras' fields of view to determine which sections are overlapping. In some embodiments, entities moving through these segments may be recognized or flagged as directed to a same physical entity by moving to a physical location and being captured by a plurality of cameras have been calibrated or trained to recognize the physical location as being directed to the same physical location.

some embodiments, the process 300 includes determining, for each of a set of entity-device pairs, whether a respective device and respective entity in entity-device pair should be associated based on a set of entity-device matching confidence factors, as indicated by block 316. In some embodiments, the entity-tracking system may determine sets of locations associated with devices and separately determine sets of locations of entities based on sets of images from cameras. The entity-tracking system may determine that the entities and devices should be associated based on the separate sets of locations and their associated measurement times. The determination of whether a device should be associated with an entity may be based on an entity-device matching confidence factor, where the entity-device matching confidence factor is indicative of the likelihood that the respective device of the entity-device pair is carried by or otherwise attached to the respective entity in the entity-device pair. Furthermore, similar to the operations described for block 308, sets of entity-device pairs may be determined and reduced using time-constrained boundaries between device locations or entity locations.

In some embodiments, as described above, the entity-tracking system may determine the location of a mobile computing device attached to an entity. For example, each row of Table 4 may be associated with a different mobile computing device and include the region captured by a field of view in which a set of mobile computing devices are located during a first duration of time "$t_1$ to $t_2$" and a second duration of time "$t_2$ to $t_3$". Further, as used in Table 4, device labels may include "PEO1," "PEO2," and "PEO3," distinct moment in time may include the labels "$t_1$," "$t_2$," and "$t_3$," and the locations captured by the field of views associated with a first camera, second camera, and third camera, respectively, may have the corresponding labels "ICS1," "ICS2," and "ICS3," respectively:

TABLE 4

| Device | Field of View in Duration $t_1$ to $t_2$ | Field of View in Duration $t_2$ to $t_3$ |
| --- | --- | --- |
| PEO1 | ICS1 | ICS2 |
| PEO2 | ICS1 | ICS3 |
| PEO3 | ICS1 | ICS1 |

Table 4 may represent data collected from a scenario during which three people walk into a monitored environment, where $t_1$=7:35 AM, $t_2$=7:45 AM, $t_3$=7:50 AM. In some embodiments, each of the labels PEO1, PEO2, or PEO3 may be determined based on device MAC addresses. The venue includes locations associated with the fields of view ICS1, ICS2, and ICS3 where each of the locations is associated with a different part of the monitored environment. For example, the location associated with ICS1 may be associated with a convention center entrance, the location associated with ICS2 may be associated with a cloak room, and the location associated with ICS3 may be associated with a lobby area. Furthermore, in this scenario, during the time period from 7:35 AM to 7:45 AM, each of the three entities holding the mobile computing devices PEO1, PEO2, or PEO3 may be in the location associated with ICS1. In this same example, during the time period from 7:45 AM to 7:50 AM, the entity holding the mobile computing device PEO1 may be in the location associated with ICS2, the entity holding the mobile computing device PEO2 may be in the location associated with ICS3, and the entity holding the mobile computing device PEO3 may be in the location associated with ICS1.

In some embodiments, the system can use a timeline matching operation to determine which entity a device should be associated with based on sensor-determined locations and locations determined from images or videos. The timeline matching operation may assign one or more scores to different possible matches of devices to entities and use the scores to determine, for a respective device, a respective entity being observed in a monitored environment. The system may use various scoring systems to compare the sets of locations determined from two different sensors. For example, some embodiments may first determine a device path based on a set of locations such as a Fréchet distance calculation to determine the similarity between two paths.

As discussed above, in some embodiments, each of the time-ordered datasets may include a measurement confidence value associated with each of the computed entity positions, where the measurement confidence value may indicate an accuracy or precision of the computed entity position. For example, a first entity position included in an images-generated time-ordered dataset may have an associated first confidence score, where the associated first measurement confidence value may a value between 0% to 100%, such as 90%, where the measurement confidence value may represent a confidence that a predicted position is within 1 meter of the computed entity position. In some embodiments, inaccuracies in camera measurements, limitations in image recognition operations, and the like may result in a less than 100% measurement confidence value in both a predicted position an predicted identity associated with an entity based on a first set of images from a first camera and a second set of images from a second camera.

In some embodiments, each of a set of measurement confidence values corresponding to device locations or entity locations may be added and then normalized such that each contribution to the measurement confidence values scales from −1 to +1, where −1 may indicate complete confidence that a device and entity are not similar, and +1 may indicate complete confidence that a device is being carried by or should otherwise be associated with the respective entity. In some embodiments, the measurement confidence value may be scaled from 0 to 1. In addition, a scoring system used to determine an entity-device matching confidence factor may also include operations to increase or decrease an entity-device matching confidence factor based on an accuracy of the channel or precision of the channel. For example, an entity position may have an associated location precision of two feet, and a scoring system may determine that the associated measurement confidence value of a 2-feet radius is 0.8. In response, the entity-device matching confidence factor may be decreased by 80%. Furthermore, in some embodiments, the average (or some other measure of centralized tendency) of a set of measurement confidence values may be computed for use when determining an entity-device matching confidence factor.

In some embodiments, the system may determine an entity-device matching confidence factor between a mobile computing device and an entity. For example, with reference to Table 1 and Table 4, each of the mobile computing devices PEO1, PEO2, and PEO3 may be compared with the path (which may be represented as a sequence of locations) taken by Entity 1 after a determination that Entity 1 should be associated with Entity 11, Entity 45, and Entity 93 for being based on the same physical entity. Based on the above, the entity-device matching confidence factors for such entity-device pairs may be represented by Table 5:

TABLE 5

| Device | Entity-Device Matching Confidence Factor (For Pairing With Entity 1) |
|---|---|
| PEO1 | 0.7 |
| PEO2 | 0.6 |
| PEO3 | 0.8 |

In some embodiments, a determination may be made that any entity-device pair having an associated entity-device matching confidence factor greater than an entity-device match threshold should be associated. For example, if the entity-device match threshold is equal to 0.65, then the entity-tracking system may determine that PEO1 and PEO3 are being carried by Entity 1. In some embodiments, for each signal-emitting device, the entity-tracking system may compare any associated entity-device match confidence factors and determine that the entity-device pair having the greatest entity-device match confidence factor should be associated. Alternatively, or in addition, this operation may be repeated for each of a set of entities detected. In some embodiments, the set of target entities may be all entities in any field of view of a camera system. Alternatively, or in addition, set of target entities may be a subset of the entities detected in a field of view.

In some embodiments, the system may determine that no match is found. For example, some embodiments may determine that an entity detected in a field of view of a first camera is not present in the field of view of any other camera at a subsequent time after determining that no confidence factor associated with other entities in other field of view's match the person. For example, a person may enter a first field of view at an entrance of a venue and then immediately depart the venue at the same entrance. In such a scenario, the entity associated with the person may have no matching entities in other field of views at a later time. In some embodiments, an entity may be explicitly tagged as having no matched entity in another field of view.

While the methods discussed above refer to an entity-device pair, similar or identical methods may be used to associate devices with each other by analyzing a set of device-device pairs. In addition, while the example above uses locations determined from EES measurements and camera measurements to determine a sequence of locations, other embodiments may use other data channels of other sensor types to determine the sequence of locations. The other channels may also result in additional attributes assigned to entities which can be used to increase the accuracy when determining that detected entities are based on a same physical entity. Example additional attributes may include body temperature attributes, chemical attributes, sound-based attributes, or the like. For example, some embodiments include associating an entity with sensor measurements from an ultrasound sensor or a set of locations determined from sensor measurements from an ultrasound sensor.

In some embodiments, the process 300 includes determining a set of sequences of locations based on the sets of locations associated with the entity pairs that should be associated and the entity-device pairs that should be associated, as indicated by block 320. Operations to determine a sequence of locations may be similar to or identical to those described for block 232 described above.

Figure 4:
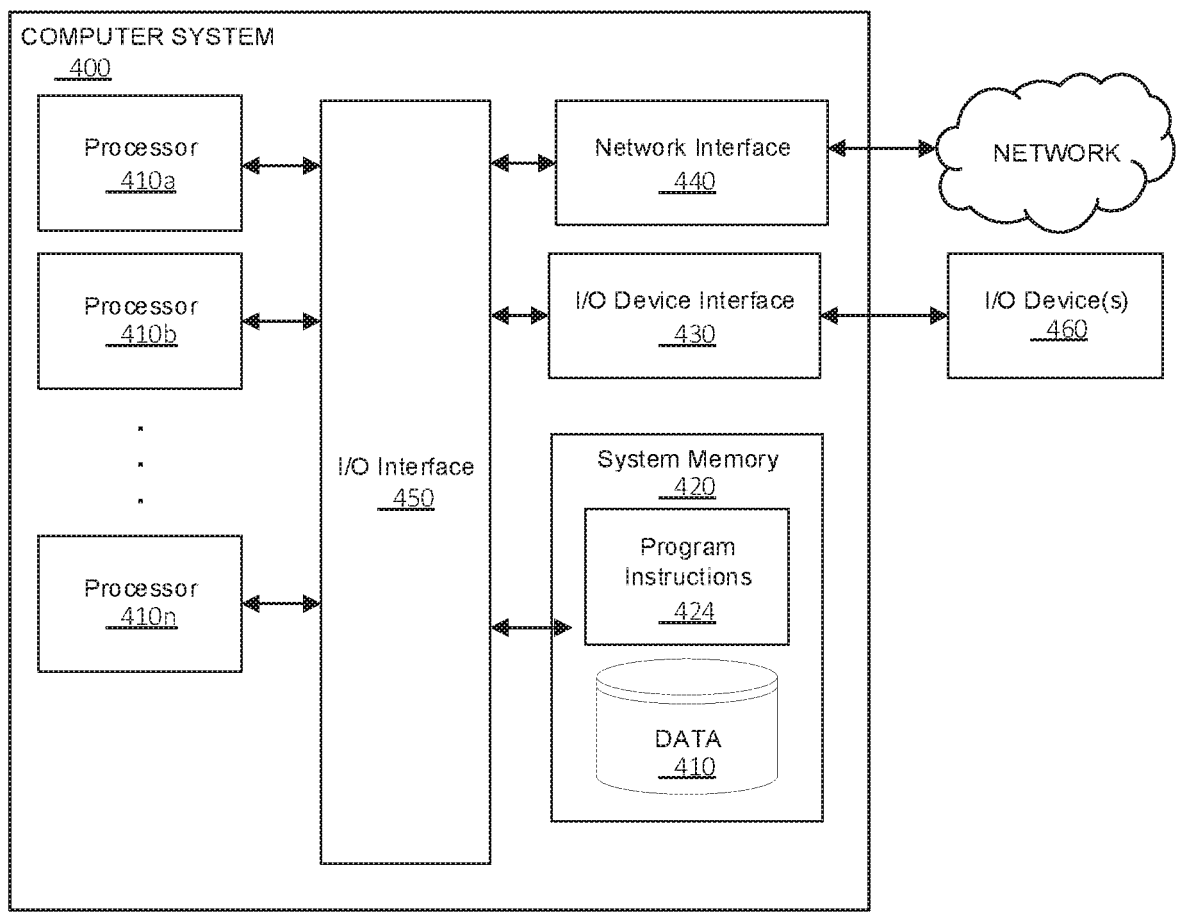
FIG. 4 shows an example of a computing device by which the present techniques may be implemented, in accordance with some embodiments.

FIG. 4 shows an example of a computer system by which the present techniques may be implemented, in accordance with some embodiments. Various portions of systems and methods described herein, may include or be executed on one or more computer systems similar to computer system 400. Further, processes and modules described herein may be executed by one or more processing systems similar to that of computer system 400.

Computer system 400 may include one or more processors (e.g., processors 410a-410n) coupled to System memory 420, an input/output I/O device interface 430, and a network interface 440 via an input/output (I/O) interface 450. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computer system 400. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may include one or more microcontrollers. A processor may receive instructions and data from a memory (e.g., System memory 420). Computer system 400 may be a uni-processor system including one processor (e.g., processor 410a), or a multi-processor system including any number of suitable processors (e.g., 410a-410n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computer system 400 may include a plurality of computing devices (e.g., distributed computer systems) to implement various processing functions.

I/O device interface 430 may provide an interface for connection of one or more I/O devices 460 to computer system 400. I/O devices may include devices that receive input (e.g., from a user) or output information (e.g., to a user). I/O devices 460 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 460 may be connected to computer system 400 through a wired or wireless connection. I/O devices 460 may be connected to computer system 400 from a remote location. I/O devices 460 located on remote computer system, for example, may be connected to computer system 400 via a network and network interface 440.

Network interface 440 may include a network adapter that provides for connection of computer system 400 to a network. Network interface may 440 may facilitate data exchange between computer system 400 and other devices connected to the network. Network interface 440 may support wired or wireless communication. The network may include an electronic communication network, such as the Internet, a local area network (LAN), a wide area network (WAN), a cellular communications network, or the like.

System memory 420 may be configured to store program instructions 424 or data 410. Program instructions 424 may be executable by a processor (e.g., one or more of processors 410a-410n) to implement one or more embodiments of the present techniques. Program instructions 424 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 420 may include a tangible program carrier having program instructions stored thereon. A tangible program carrier may include a non-transitory, computer-readable storage medium. A non-transitory, computer-readable storage medium may include a machine readable storage device, a machine readable storage substrate, a memory device, or any combination thereof. Non-transitory, computer-readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 420 may include a non-transitory, computer-readable storage medium that may have program instructions stored thereon that are executable by a computer processor (e.g., one or more of processors 410a-410n) to cause the subject matter and the functional operations described herein. A memory (e.g., System memory 420) may include a single memory device and/or a plurality of memory devices (e.g., distributed memory devices). Instructions or other program code to provide the functionality described herein may be stored on a tangible, non-transitory, computer-readable media. In some cases, the entire set of instructions may be stored concurrently on the media, or in some cases, different parts of the instructions may be stored on the same media at different times.

I/O interface 450 may be configured to coordinate I/O traffic between processors 410a-410n, System memory 420, network interface 440, I/O devices 460, and/or other peripheral devices. I/O interface 450 may perform protocol, timing, or other data transformations to convert data signals from one component (e.g., System memory 420) into a format suitable for use by another component (e.g., processors 410a-410n). I/O interface 450 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 400 or multiple computer systems 400 configured to host different portions or instances of embodiments. Multiple computer systems 400 may provide for parallel or sequential processing/execution of one or more portions of the techniques described herein.

Those skilled in the art will appreciate that computer system 400 is merely illustrative and is not intended to limit the scope of the techniques described herein. Computer system 400 may include any combination of devices or software that may perform or otherwise provide for the performance of the techniques described herein. For example, computer system 400 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a GPS device, or the like. Computer system 400 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 400 may be transmitted to computer system 400 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The word "set" when used as a noun include a single item or a plurality of items, such that the phrase "set of items" may refer to either a single item or multiple items. The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A non-transitory, machine-readable medium storing instructions that, when executed by one or more processors, effectuate operations comprising acquiring, using a computer system, a set of images from a plurality of cameras, wherein each of the plurality of cameras have a different respective field of view, and at least part of the fields of view are of a monitored environment; detecting and localizing, using the computer system, in at least some of the set of images, a first entity moving through the monitored environment; determining, using the computer system, a first set of locations within the monitored environment of the first entity based on locations of the first entity in the set of images, wherein each of the first set of locations is associated with an image acquisition time; acquiring, using the computer system, a set of sensor measurements of the monitored environment from a plurality of sensors, the plurality of sensors being different from the plurality of cameras; determining, using the computer system, a second set of locations within the monitored environment of the first entity based on the set of sensor measurements, wherein each of the second set of locations is associated with a sensor measurement time; determining, using the computer system, whether the first set of locations should be associated with the second set of locations based on a set of confidence factors calculated based on the first set of locations and the second set of locations, the set of confidence factors being indicative of the second set of locations being locations of the first entity and not another entity; in response to determining that the first set of locations should be associated with the second set of locations, determining, using the computer system, a sequence of locations of the first entity through the monitored environment; and storing, using the computer system, the sequence of locations in a computer-readable media in communication with the computer system.

2. The medium of embodiment 1, wherein a first subset of the set of images is acquired by a first camera and a second subset of the set of images is acquired by a second camera, and wherein determining the first entity comprises detecting, using the computer system, the first entity based on the first subset of the set of images using a convolutional neural network; determining, using the computer system, a first set of attributes associated with the first entity based on the first subset of the set of images; detecting, using the computer system, a second entity based on the second subset of the set of images using the convolutional neural network; determining, using the computer system, a second set of attributes associated with the second entity based on the second subset of the set of images; determining, using the computer system, a matching entity confidence factor, wherein the matching entity confidence factor is based on the first set of attributes and the second set of attributes; and associating the first entity with the second entity based on the matching entity confidence factor.

3. The medium of embodiment 2, wherein the first set of attributes comprises a first gait attribute associated with the first entity, wherein determining the first set of attributes comprises determining the first gait attribute based on the first subset of the set of images, and wherein the first gait attribute comprises at least one of a movement speed, postural sway, stride frequency, gait symmetry, gait dynamic range, or gait characteristic curve; and the second set of attributes comprises a second gait attribute associated with the second entity, wherein determining the second set of attributes comprises determining the second gait attribute based on the second subset of the set of images, wherein the second gait attribute comprises a same attribute type as the first gait attribute.

4. The medium of embodiments 2 to 3, wherein determining the matching entity confidence factor comprises using a first image comprising a portion of the first entity and a second image comprising a portion of the second entity as inputs for a capsule neural network.

5. The medium of embodiments 2 to 4, wherein determining the matching entity confidence factor comprises using a siamese neural network to determine the matching entity confidence factor, wherein the siamese neural network is trained using a first image comprising a portion of the first entity, and wherein using the siamese neural network comprises using a second image comprising a portion of the second entity as inputs.

6. The medium of embodiments 2 to 5, wherein the operations further comprises determining a boundary of the first entity with respect to a first location, wherein the first entity is detected to be at the first location at a first measurement time, and wherein the boundary is determined based on the first location and a time difference between the first measurement time and a second measurement time; and wherein determining the matching entity confidence factor comprises determining the matching entity confidence factor based on a distance between the boundary and a second location, wherein the second entity is determined to be at the second location at a second measurement time, wherein the second measurement time is after the first measurement time.

7. The medium of embodiments 2 to 6, wherein the operations further comprises determining a boundary of the first entity with respect to a first location, wherein the first entity is detected to be at the first location at a first measurement time, and wherein the boundary is determined based on the first location and a time difference between the first measurement time and a second measurement time; and determining that a field of view of the second camera is within the boundary.

8. The medium of embodiments 1 to 7, wherein detecting and localizing the first entity comprises determining an attention weight, wherein the attention weight is based on the detection of an attribute associated with the first entity, and wherein the attention weight is used by a neural network to determine the set of confidence factors.

9. The medium of embodiments 1 to 8, wherein detecting and localizing the first entity comprises segmenting a first image of the set of images into a set of grid cells; for each respective grid cell of the set of grid cells, determining a bounding box associated with the respective grid cell using a convolution operation; and detecting the entity based on the bounding box.

10. The medium of embodiments 1 to 9, wherein detecting the first entity comprises determining a set visual features in a first image of the set of images and a set of visual feature positions associated with the set of visual features; generating a set of bounding boxes for each of the set of features, wherein each of the set of bounding boxes encloses one of the set of feature positions using a convolutional operation; for each respective bounding box in the set of bounding boxes, determine a respective class score based on a portion of the first image bounded by the respective bounding box using a convolution operation, wherein the respective class score is associated with a first object type in a set of object types, and wherein the respective class score is indicative of a likelihood that the respective bounding box is bounding an object of the object type; and detecting the first entity based on the set of bounding boxes and a set of class scores comprising the respective class scores.

11. The medium of embodiments 1 to 10, wherein determining the sequence of locations of the first entity through the monitored environment the operations further comprises applying a Kalman filter to determine the sequence of locations based on the second set of locations.

12. The medium of embodiments 1 to 11, wherein the plurality of sensors is a first plurality of sensors, and wherein the operations further comprising acquiring, using the computer system, a second set of sensor measurements of the monitored environment from a second plurality of sensors, wherein the second plurality of sensors are different from the plurality of cameras, and wherein the second plurality of sensors are different from the first plurality of sensors; determining, using the computer system, a third set of locations within the monitored environment of the first entity based on the second set of sensor measurements, wherein each of the third set of locations is associated with the sensor measurement time, wherein determining the sequence of locations of the first entity comprises determining the sequence of locations of the first entity based on the third set of locations.

13. The medium of embodiments 1 to 12, wherein the plurality of sensors comprises electronic emission sensors, and wherein determining the sequence of locations comprises determining a location based on a time of arrival of a signal from a mobile computing device or an angle of arrival of the signal from the mobile computing device.

14. The medium of embodiments 1 to 13, wherein the plurality of sensors comprises a temperature sensor, and wherein the operations further comprise determining an entity temperature of the first entity using the temperature sensor, wherein the entity temperature is measured at a first time of measurement; and determining an entity location associated with the entity temperature at the first time of measurement, wherein the second set of locations comprises the entity location.

15. The medium of embodiments 1 to 14, wherein the plurality of sensors comprises a chemical sensor, and wherein the operations further comprise determining a volatile chemical signature of the first entity using the chemical sensor, wherein the volatile chemical signature is measured at a first time of measurement; and determining an entity location associated with the volatile chemical signature at the first time of measurement, wherein the second set of locations comprises the entity location.

16. The medium of embodiments 1 to 15, wherein the plurality of sensors comprises an ultrasonic sound sensor, and wherein the operations further comprise determining a sound of the first entity using the ultrasonic sound sensor, wherein the sound is measured at a first time of measurement; and determining an entity location associated with the sound at the first time of measurement, wherein the second set of locations comprises the entity location.

17. The medium of embodiments 1 to 16, wherein a sensor of the plurality of sensors is attached to a camera of the plurality of cameras.

18. The medium of embodiments 1 to 17, further comprising determining, using the computer system, whether a location in the sequence of locations is in a restricted area of the monitored environment; and in response to a determination that the location is in the restricted area of the monitored environment, display a warning to a graphical display device.

19. The medium of embodiments 1 to 18, further comprising determining, using the computer system, whether a location in the sequence of locations is outside a permitted area of the monitored environment; and in response to a determination that the location is outside the permitted area of the monitored environment, display a warning to a graphical display device.

20. A method comprising acquiring, using a computer system, a set of images from a plurality of cameras, wherein each of the plurality of cameras have a different respective field of view, and at least part of the fields of view are of a monitored environment; detecting and localizing, using the computer system, in at least some of the set of images, a first entity moving through the monitored environment; determining, using the computer system, a first set of locations within the monitored environment of the first entity based on locations of the first entity in the set of images, wherein each of the first set of locations is associated with an image acquisition time; acquiring, using the computer system, a set of sensor measurements of the monitored environment from a plurality of sensors, the plurality of sensors being different from the plurality of cameras; determining, using the computer system, a second set of locations within the monitored environment of the first entity based on the set of sensor measurements, wherein each of the second set of locations is associated with a sensor measurement time; determining, using the computer system, whether the first set of locations should be associated with the second set of locations based on a set of confidence factors calculated based on the first set of locations and the second set of locations, the set of confidence factors being indicative of the second set of locations being locations of the first entity and not another entity; in response to determining that the first set of locations should be associated with the second set of locations, determining, using the computer system, a sequence of locations of the first entity through the monitored environment; and storing, using the computer system, the sequence of locations in a computer-readable media in communication with the computer system.

What is claimed is:

1. A non-transitory, machine-readable medium storing instructions that, when executed by one or more processors, effectuate operations comprising:
   acquiring, using a computer system, a set of images from a plurality of cameras, wherein:
      each of the plurality of cameras have a different respective field of view, and
      at least part of the fields of view are of a monitored environment;
   detecting and localizing, using the computer system, in at least some of the set of images, a first entity moving through the monitored environment;
   determining, using the computer system, a first set of locations within the monitored environment of the first entity based on locations of the first entity in the set of images, wherein each of the first set of locations is associated with an image acquisition time;
   acquiring, using the computer system, a set of sensor measurements of the monitored environment from a plurality of sensors, the plurality of sensors being different from the plurality of cameras;
   determining, using the computer system, a second set of locations within the monitored environment of the first entity based on the set of sensor measurements, wherein each of the second set of locations is associated with a sensor measurement time;
   determining, using the computer system, whether the first set of locations should be associated with the second set of locations based on a set of confidence factors calculated based on the first set of locations and the second set of locations, the set of confidence factors being indicative of the second set of locations being locations of the first entity and not another entity;
   in response to determining that the first set of locations should be associated with the second set of locations, determining, using the computer system, a sequence of locations of the first entity through the monitored environment; and
   storing, using the computer system, the sequence of locations in a computer-readable media in communication with the computer system, wherein a first subset of the set of images is acquired by a first camera and a second subset of the set of images is acquired by a second camera, and wherein determining the first entity comprises:
      detecting, using the computer system, the first entity based on the first subset of the set of images using a convolutional neural network;
      determining, using the computer system, a first set of attributes associated with the first entity based on the first subset of the set of images;
      detecting, using the computer system, a second entity based on the second subset of the set of images using the convolutional neural network;
      determining, using the computer system, a second set of attributes associated with the second entity based on the second subset of the set of images;
      determining, using the computer system, a matching entity confidence factor, wherein the matching entity confidence factor is based on the first set of attributes and the second set of attributes; and
      associating the first entity with the second entity based on the matching entity confidence factor.

2. The medium of claim 1, wherein:
   the first set of attributes comprises a first gait attribute associated with the first entity, wherein determining the first set of attributes comprises determining the first gait attribute based on the first subset of the set of images, and wherein the first gait attribute comprises at least one of a movement speed, postural sway, stride frequency, gait symmetry, gait dynamic range, or gait characteristic curve; and
   the second set of attributes comprises a second gait attribute associated with the second entity, wherein determining the second set of attributes comprises determining the second gait attribute based on the second subset of the set of images, wherein the second gait attribute comprises a same attribute type as the first gait attribute.

3. The medium of claim 1, wherein determining the matching entity confidence factor comprises using a first image comprising a portion of the first entity and a second image comprising a portion of the second entity as inputs for a capsule neural network.

4. The medium of claim 1, wherein determining the matching entity confidence factor comprises using a siamese neural network to determine the matching entity confidence factor, wherein the siamese neural network is trained using a first image comprising a portion of the first entity, and wherein using the siamese neural network comprises using a second image comprising a portion of the second entity as inputs.

5. The medium of claim 1, wherein the operations further comprises:
   determining a boundary of the first entity with respect to a first location, wherein the first entity is detected to be at the first location at a first measurement time, and wherein the boundary is determined based on the first location and a time difference between the first measurement time and a second measurement time; and
   wherein determining the matching entity confidence factor comprises determining the matching entity confidence factor based on a distance between the boundary and a second location, wherein the second entity is determined to be at the second location at a second measurement time, wherein the second measurement time is after the first measurement time.

6. The medium of claim 1, wherein the operations further comprises:
   determining a boundary of the first entity with respect to a first location, wherein the first entity is detected to be at the first location at a first measurement time, and wherein the boundary is determined based on the first location and a time difference between the first measurement time and a second measurement time; and
   determining that a field of view of the second camera is within the boundary.

7. The medium of claim 1, wherein detecting and localizing the first entity comprises determining an attention weight, wherein the attention weight is based on the detection of an attribute associated with the first entity, and wherein the attention weight is used by a neural network to determine the set of confidence factors.

8. The medium of claim 1, wherein detecting and localizing the first entity comprises:
- segmenting a first image of the set of images into a set of grid cells;
- for each respective grid cell of the set of grid cells, determining a bounding box associated with the respective grid cell using a convolution operation; and
- detecting the entity based on the bounding box.

9. The medium of claim 1, wherein detecting the first entity comprises:
- determining a set visual features in a first image of the set of images and a set of visual feature positions associated with the set of visual features;
- generating a set of bounding boxes for each of the set of features, wherein each of the set of bounding boxes encloses one of the set of feature positions using a convolutional operation;
- for each respective bounding box in the set of bounding boxes, determine a respective class score based on a portion of the first image bounded by the respective bounding box using a convolution operation, wherein the respective class score is associated with a first object type in a set of object types, and wherein the respective class score is indicative of a likelihood that the respective bounding box is bounding an object of the object type; and
- detecting the first entity based on the set of bounding boxes and a set of class scores comprising the respective class scores.

10. The medium of claim 1, wherein determining the sequence of locations of the first entity through the monitored environment the operations further comprises applying a Kalman filter to determine the sequence of locations based on the second set of locations.

11. The medium of claim 1, wherein the plurality of sensors is a first plurality of sensors, and wherein the operations further comprising:
- acquiring, using the computer system, a second set of sensor measurements of the monitored environment from a second plurality of sensors, wherein the second plurality of sensors are different from the plurality of cameras, and wherein the second plurality of sensors are different from the first plurality of sensors;
- determining, using the computer system, a third set of locations within the monitored environment of the first entity based on the second set of sensor measurements, wherein each of the third set of locations is associated with the sensor measurement time, wherein determining the sequence of locations of the first entity comprises determining the sequence of locations of the first entity based on the third set of locations.

12. The medium of claim 1, wherein the plurality of sensors comprises electronic emission sensors, and wherein determining the sequence of locations comprises determining a location based on a time of arrival of a signal from a mobile computing device or an angle of arrival of the signal from the mobile computing device.

13. The medium of claim 1, wherein the plurality of sensors comprises a temperature sensor, and wherein the operations further comprise:
- determining an entity temperature of the first entity using the temperature sensor, wherein the entity temperature is measured at a first time of measurement; and
- determining an entity location associated with the entity temperature at the first time of measurement, wherein the second set of locations comprises the entity location.

14. The medium of claim 1, wherein the plurality of sensors comprises a chemical sensor, and wherein the operations further comprise:
- determining a volatile chemical signature of the first entity using the chemical sensor, wherein the volatile chemical signature is measured at a first time of measurement; and
- determining an entity location associated with the volatile chemical signature at the first time of measurement, wherein the second set of locations comprises the entity location.

15. The medium of claim 1, wherein the plurality of sensors comprises an ultrasonic sound sensor, and wherein the operations further comprise:
- determining a sound of the first entity using the ultrasonic sound sensor, wherein the sound is measured at a first time of measurement; and
- determining an entity location associated with the sound at the first time of measurement, wherein the second set of locations comprises the entity location.

16. The medium of claim 1, wherein a sensor of the plurality of sensors is attached to a camera of the plurality of cameras.

17. The medium of claim 1, the operations further comprising:
- determining, using the computer system, whether a location in the sequence of locations is in a restricted area of the monitored environment; and
- in response to a determination that the location is in the restricted area of the monitored environment, display a warning to a graphical display device.

18. The medium of claim 1, the operations further comprising:
- determining, using the computer system, whether a location in the sequence of locations is outside a permitted area of the monitored environment; and
- in response to a determination that the location is outside the permitted area of the monitored environment, display a warning to a graphical display device.

19. The medium of claim 1, wherein:
- the first set of attributes comprises a first gait attribute associated with the first entity, wherein determining the first set of attributes comprises determining the first gait attribute based on the first subset of the set of images, and wherein the first gait attribute comprises at least one of a movement speed, postural sway, stride frequency, gait symmetry, gait dynamic range, or gait characteristic curve; and
- the second set of attributes comprises a second gait attribute associated with the second entity, wherein determining the second set of attributes comprises determining the second gait attribute based on the second subset of the set of images, wherein the second gait attribute comprises a same attribute type as the first gait attribute;
- the operations further comprises determining a boundary of the first entity with respect to a first location, wherein the first entity is detected to be at the first location at a first measurement time, and wherein the boundary is determined based on the first location and a time difference between the first measurement time and a second measurement time; and
- determining the matching entity confidence factor comprises determining the matching entity confidence factor based on a distance between the boundary and a second location, wherein the second entity is determined to be at the second location at a second measurement time, wherein the second measurement time is after the first measurement time.

20. The medium of claim 1, wherein the operations comprise:
steps for mitigating data sparseness issues when detecting and localizing entities.

21. The medium of claim 1, wherein the operations comprise:
steps for mitigating determining attributes of entities.

22. The medium of claim 1, wherein the operations comprise:
steps for determining confidence values.

23. A method comprising:
acquiring, using a computer system, a set of images from a plurality of cameras, wherein:
each of the plurality of cameras have a different respective field of view, and
at least part of the fields of view are of a monitored environment;
detecting and localizing, using the computer system, in at least some of the set of images, a first entity moving through the monitored environment;
determining, using the computer system, a first set of locations within the monitored environment of the first entity based on locations of the first entity in the set of images, wherein each of the first set of locations is associated with an image acquisition time;
acquiring, using the computer system, a set of sensor measurements of the monitored environment from a plurality of sensors, the plurality of sensors being different from the plurality of cameras;
determining, using the computer system, a second set of locations within the monitored environment of the first entity based on the set of sensor measurements, wherein each of the second set of locations is associated with a sensor measurement time;
determining, using the computer system, whether the first set of locations should be associated with the second set of locations based on a set of confidence factors calculated based on the first set of locations and the second set of locations, the set of confidence factors being indicative of the second set of locations being locations of the first entity and not another entity;
in response to determining that the first set of locations should be associated with the second set of locations, determining, using the computer system, a sequence of locations of the first entity through the monitored environment; and
storing, using the computer system, the sequence of locations in a computer-readable media in communication with the computer system, wherein a first subset of the set of images is acquired by a first camera and a second subset of the set of images is acquired by a second camera, and wherein determining the first entity comprises:
detecting, using the computer system, the first entity based on the first subset of the set of images using a convolutional neural network;
determining, using the computer system, a first set of attributes associated with the first entity based on the first subset of the set of images;
detecting, using the computer system, a second entity based on the second subset of the set of images using the convolutional neural network;
determining, using the computer system, a second set of attributes associated with the second entity based on the second subset of the set of images;
determining, using the computer system, a matching entity confidence factor, wherein the matching entity confidence factor is based on the first set of attributes and the second set of attributes; and
associating the first entity with the second entity based on the matching entity confidence factor.

24. The method of claim 23, wherein:
the first set of attributes comprises a first gait attribute associated with the first entity, wherein determining the first set of attributes comprises determining the first gait attribute based on the first subset of the set of images, and wherein the first gait attribute comprises at least one of a movement speed, postural sway, stride frequency, gait symmetry, gait dynamic range, or gait characteristic curve; and
the second set of attributes comprises a second gait attribute associated with the second entity, wherein determining the second set of attributes comprises determining the second gait attribute based on the second subset of the set of images, wherein the second gait attribute comprises a same attribute type as the first gait attribute.

25. The method of claim 23, wherein determining the matching entity confidence factor comprises using a first image comprising a portion of the first entity and a second image comprising a portion of the second entity as inputs for a capsule neural network.

26. The method of claim 23, wherein determining the matching entity confidence factor comprises using a siamese neural network to determine the matching entity confidence factor, wherein the siamese neural network is trained using a first image comprising a portion of the first entity, and wherein using the siamese neural network comprises using a second image comprising a portion of the second entity as inputs.

27. The method of claim 23, comprising:
determining a boundary of the first entity with respect to a first location, wherein the first entity is detected to be at the first location at a first measurement time, and wherein the boundary is determined based on the first location and a time difference between the first measurement time and a second measurement time; and
wherein determining the matching entity confidence factor comprises determining the matching entity confidence factor based on a distance between the boundary and a second location, wherein the second entity is determined to be at the second location at a second measurement time, wherein the second measurement time is after the first measurement time.

28. The method of claim 23, comprising:
determining a boundary of the first entity with respect to a first location, wherein the first entity is detected to be at the first location at a first measurement time, and wherein the boundary is determined based on the first location and a time difference between the first measurement time and a second measurement time; and
determining that a field of view of the second camera is within the boundary.

29. The method of claim 23, wherein detecting and localizing the first entity comprises determining an attention weight, wherein the attention weight is based on the detection of an attribute associated with the first entity, and wherein the attention weight is used by a neural network to determine the set of confidence factors.

30. The method of claim 23, wherein detecting and localizing the first entity comprises:

segmenting a first image of the set of images into a set of grid cells;

for each respective grid cell of the set of grid cells, determining a bounding box associated with the respective grid cell using a convolution operation; and detecting the entity based on the bounding box.

31. The method of claim 23, wherein detecting the first entity comprises:

determining a set visual features in a first image of the set of images and a set of visual feature positions associated with the set of visual features;

generating a set of bounding boxes for each of the set of features, wherein each of the set of bounding boxes encloses one of the set of feature positions using a convolutional operation;

for each respective bounding box in the set of bounding boxes, determine a respective class score based on a portion of the first image bounded by the respective bounding box using a convolution operation, wherein the respective class score is associated with a first object type in a set of object types, and wherein the respective class score is indicative of a likelihood that the respective bounding box is bounding an object of the object type; and detecting the first entity based on the set of bounding boxes and a set of class scores comprising the respective class scores.

32. The method of claim 23, wherein determining the sequence of locations of the first entity through the monitored environment further comprises applying a Kalman filter to determine the sequence of locations based on the second set of locations.

33. The method of claim 23, wherein the plurality of sensors is a first plurality of sensors, and the method further comprises:

acquiring, using the computer system, a second set of sensor measurements of the monitored environment from a second plurality of sensors, wherein the second plurality of sensors are different from the plurality of cameras, and wherein the second plurality of sensors are different from the first plurality of sensors;

determining, using the computer system, a third set of locations within the monitored environment of the first entity based on the second set of sensor measurements, wherein each of the third set of locations is associated with the sensor measurement time, wherein determining the sequence of locations of the first entity comprises determining the sequence of locations of the first entity based on the third set of locations.

34. The method of claim 23, wherein the plurality of sensors comprises electronic emission sensors, and wherein determining the sequence of locations comprises determining a location based on a time of arrival of a signal from a mobile computing device or an angle of arrival of the signal from the mobile computing device.

35. The method of claim 23, wherein the plurality of sensors comprises a temperature sensor, and wherein the method further comprises:

determining an entity temperature of the first entity using the temperature sensor, wherein the entity temperature is measured at a first time of measurement; and determining an entity location associated with the entity temperature at the first time of measurement, wherein the second set of locations comprises the entity location.

36. The method of claim 23, wherein the plurality of sensors comprises a chemical sensor, and wherein the method further comprises:

determining a volatile chemical signature of the first entity using the chemical sensor, wherein the volatile chemical signature is measured at a first time of measurement; and determining an entity location associated with the volatile chemical signature at the first time of measurement, wherein the second set of locations comprises the entity location.

37. The method of claim 23, wherein the plurality of sensors comprises an ultrasonic sound sensor, and wherein the method further comprises:

determining a sound of the first entity using the ultrasonic sound sensor, wherein the sound is measured at a first time of measurement; and determining an entity location associated with the sound at the first time of measurement, wherein the second set of locations comprises the entity location.

38. The method of claim 23, wherein a sensor of the plurality of sensors is attached to a camera of the plurality of cameras.

39. The method of claim 23, further comprising:

determining, using the computer system, whether a location in the sequence of locations is in a restricted area of the monitored environment; and in response to a determination that the location is in the restricted area of the monitored environment, display a warning to a graphical display device.

40. The method of claim 23, further comprising:

determining, using the computer system, whether a location in the sequence of locations is outside a permitted area of the monitored environment; and in response to a determination that the location is outside the permitted area of the monitored environment, display a warning to a graphical display device.

41. The method of claim 23, wherein:

the first set of attributes comprises a first gait attribute associated with the first entity, wherein determining the first set of attributes comprises determining the first gait attribute based on the first subset of the set of images, and wherein the first gait attribute comprises at least one of a movement speed, postural sway, stride frequency, gait symmetry, gait dynamic range, or gait characteristic curve; and the second set of attributes comprises a second gait attribute associated with the second entity, wherein determining the second set of attributes comprises determining the second gait attribute based on the second subset of the set of images, wherein the second gait attribute comprises a same attribute type as the first gait attribute;

the method further comprises determining a boundary of the first entity with respect to a first location, wherein the first entity is detected to be at the first location at a first measurement time, and wherein the boundary is determined based on the first location and a time difference between the first measurement time and a second measurement time; and determining the matching entity confidence factor comprises determining the matching entity confidence factor based on a distance between the boundary and a second location, wherein the second entity is determined to be at the second location at a second measurement time, wherein the second measurement time is after the first measurement time.

42. The method of claim 23, comprising: steps for mitigating data sparseness issues when detecting and localizing entities.

43. The method of claim 23, comprising: steps for mitigating determining attributes of entities.

44. The method of claim 23, comprising: steps for determining confidence values.

* * * * *